(12) United States Patent
Pasquale et al.

(10) Patent No.: US 7,999,069 B2
(45) Date of Patent: Aug. 16, 2011

(54) EPHB RECEPTOR-BINDING PEPTIDES

(75) Inventors: Elena B. Pasquale, La Jolla, CA (US); Mitchell Koolpe, Palo Alto, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 0 days.

(21) Appl. No.: 12/549,953

(22) Filed: Aug. 28, 2009

(65) Prior Publication Data

US 2010/0183510 A1 Jul. 22, 2010

Related U.S. Application Data

(63) Continuation of application No. 11/342,247, filed on Jan. 26, 2006, now Pat. No. 7,582,438.

(60) Provisional application No. 60/647,852, filed on Jan. 27, 2005.

(51) Int. Cl.
*A61K 38/04* (2006.01)
(52) U.S. Cl. ......... 530/324; 530/325; 530/326; 530/327
(58) Field of Classification Search ........................ None
See application file for complete search history.

(56) References Cited

U.S. PATENT DOCUMENTS

| | | | |
|---|---|---|---|
| 5,512,457 | A | 4/1996 | Lyman et al. |
| 5,516,658 | A | 5/1996 | Beckmann et al. |
| 5,624,899 | A | 4/1997 | Bennett et al. |
| 5,627,267 | A | 5/1997 | Lyman et al. |
| 5,650,504 | A | 7/1997 | Bartley et al. |
| 5,716,934 | A | 2/1998 | Bartley et al. |
| 5,738,844 | A | 4/1998 | Beckmann et al. |
| 5,795,734 | A | 8/1998 | Flanagan et al. |
| 5,798,448 | A | 8/1998 | Caras et al. |
| 5,824,303 | A | 10/1998 | Bartley et al. |
| 6,001,964 | A | 12/1999 | Gaynor et al. |
| 6,864,227 | B1 | 3/2005 | Wang et al. |
| 2004/0180823 | A1 | 9/2004 | Pasquale et al. |
| 2004/0247592 | A1 | 12/2004 | Roifman et al. |

FOREIGN PATENT DOCUMENTS

| | | |
|---|---|---|
| WO | WO90/00192 | 1/1990 |
| WO | WO94/11020 | 5/1994 |
| WO | WO95/06065 | 3/1995 |
| WO | WO96/01839 | 1/1996 |
| WO | WO96/02645 | 2/1996 |
| WO | WO96/09384 | 3/1996 |
| WO | WO96/10911 | 4/1996 |
| WO | WO96/13518 | 5/1996 |
| WO | WO96/17925 | 6/1996 |
| WO | WO96/23000 | 8/1996 |
| WO | WO96/26958 | 9/1996 |
| WO | WO96/36713 | 11/1996 |
| WO | WO97/36919 | 10/1997 |
| WO | WO99/08696 | 2/1999 |
| WO | WO99/10495 | 3/1999 |
| WO | WO99/45121 | 9/1999 |
| WO | WO99/52541 | 10/1999 |
| WO | WO99/67285 | 12/1999 |
| WO | WO00/30673 | 6/2000 |
| WO | WO00/37500 | 6/2000 |
| WO | WO01/08636 | 2/2001 |
| WO | WO02/26827 | 4/2002 |
| WO | WO2004/028551 | 4/2004 |
| WO | WO2004/080425 | 9/2004 |
| WO | WO2004/091375 | 10/2004 |
| WO | WO2006/081418 | 8/2006 |
| WO | WO2008/100288 | 8/2008 |

OTHER PUBLICATIONS

Pasquale E.B., Eph—ephrin promiscuity is now crystal clear. *Nature Neuroscience* 7, 417-418 (2004).*
U.S. Appl. No. 60/647,852, filed Jan. 27, 2005, Pasquale, et al.
Aasland, et al., "Normalization of nomenclature for peptide motifs as ligands of modular protein domains" *FEBS Lett.* (2002) 513(1): 141-144.
Adams, et al., "Eph receptors and ephrin ligands: essential mediators of vascular development" *Trends Cardiovasc. Med.* (2004) 10(5): 183-188.
Andrews, et al., "Expression of two novel eph-related receptor protein tyrosine kinases in mammary gland development and carcinogenesis" *Oncogene* (1994) 9: 1461-1467.
Aoki, et al., "Eph receptors direct the differentiation of mammalian neural precursor cells through a mitogen-activated protein kinase-dependent pathway" *J. Biol. Chem.* (2004) 279(31): 32643-32650.
Arap, et al., "Cancer treatment by targeted drug delivery to tumor vasculature in a mouse model" *Science* (1998) 279(5349): 377-380.
Arap, et al., "Targeting the prostate for destruction through a vascular address" *PNAS USA* (2002) 99(3): 1527-1531.
Batlle, et al., "EphB receptor activity suppresses colorectal cancer progression" *Nature* (2005) 435: 1126-1130.
Battaglia, et al., "EphB receptors and ephrin-B ligands regulate spinal sensory connectivity and modulate pain processing" *Nat. Neurosci.* (2003) 6(4): 339-340.
Bennett, et al., "Molecular cloning of a ligand for the EPH-related receptor protein-tyrosine kinase Htk" *PNAS USA* (1995) 92(6): 1866-1870.
Blanco, et al., "Formation and stability of beta-hairpin structures in polypeptides" *Curr. Opin. Struct. Biol.* (1998) 8(1): 107-111.
Bork et al., "Go hunting in sequence database but watch out for the traps" *Trends in Genetics* (1996) 12(10): 425-427.
Bork, "Powers and pitfalls in sequence analysis: The 70% hurdle" *Genome Res.* (2000) 102: 398-400.
Brantely-Sieders, et al., "Eph receptor tyrosine kinases in angiogenesis: form development to disease" *Angiogenesis* (2004) 7(1): 17-28.
Brantely-Sieders, et al., "Eph receptor tyrosine kinases in tumor and tumor microenvironment" *Curr Pharma Design* (2004) 10: 3431-3442.

(Continued)

Primary Examiner — Maher M Haddad
(74) Attorney, Agent, or Firm — Knobbe Martens Olson & Bear LLP

(57) ABSTRACT

The application is related to the identification of peptides that selectively bind to Eph receptors of the B class. Also disclosed are uses of such peptides in the treatment of a variety of diseases. Additionally, imaging tumors in patients is described by administrating labeled peptides to patients and then obtaining an image of the labeled peptides.

15 Claims, 6 Drawing Sheets

OTHER PUBLICATIONS

Brenner, "Errors in genome functions" *Trends in Genetics* (1999) 15(4): 132-133.
Carles-Kinch, et al., "Antibody targeting of the EphA2 tyrosine kinase inhibits malignant cell behavior" *Cancer Res.* (2002) 62(10): 2840-2847.
Chang, et al., (1986) NCBI Accession No. P01153, p. 1. [retrieved on Feb. 3, 2006]. Retrieved from the Internet: <http://www.ncbi.nlm.nih.gov/entrez/viewer.fcgi?db=protein&val=123907>.
Chrencik, et al., "Structure and Biophyscial Characterization of the EphB4-EphrinB2 Protein-Protein Interaction and Receptor Specificity" *J. Biol. Chem.* (2006) 281(38): 28185-28192.
Chrencik, et al., "Structure and thermodynamic characterization of the EphB4/Ephrin-B2 antagonist peptide complex reveals the determinants for receptor specificity" *Structure* (2006) 14(2): 321-330.
Conover, et al., "Disruption of Eph/ephrin signaling affects migration and proliferation in the adult subventricular zone" *Nat. Neurosci.* (2000) 3(11): 1091-1097.
Cwirla, et al., "Peptide agonist of the thrombopoietin receptor as potent as the natural cytokine" *Science* (1997) 276(5319): 1696-1699.
Dail, et al., "Eph receptors inactivate-R-Ras through different mechanisms to achieve cell repulsion" *J. Cell Sci.* (2006) 119(Pt. 7): 1244-1254.
Daniel, et al., "ELK and LERK-2 in developing kidney and microvascular endothelial assembly" *Kidney Int. Suppl.* (1996) 57: S73-S81.
Davis, et al., "Ligands for EPH-related receptor tyrosine kinases that require membrane attachment or clustering for activity" *Science* (1994) 266(5186): 816-819.
Devlin, et al., "Random peptide libraries: a source of specific protein binding molecules" *Science* (1990) 249: 404-406.
Dodelet, et al., "Eph receptors and ephrin ligands: embryogenesis to tumorigenesis" *Oncogene* (2000) 19(49): 5614-5619.
Doerks, et al., "Protein annotation' detective work for function prediction" *Trends in Genetics* (1998) 14(6): 248-250.
Dohn, et al., "Receptor tyrosine kinase EphA2 is regulated by p53-family proteins and induces apoptosis" *Oncogene* (2001) 20(45): 6503-6515.
Dottori, et al., "EphA4 (Sek1) receptor tyrosine kinase is required for the development of the corticospinal tract" *PNAS USA* (1998) 95: 13248-13253.
Dvorak, et al., "Identification and characterization of the blood vessels of solid tumors that are leaky to circulating macromolecules" *Am. J. Pathol.* (1988) 133: 95-109.
Dybwad, et al., "Increased serum and synovial fluid antibodies to immunoselected peptides in patients with rheumatoid arthritis" *Annals of Rheumatoid Diseases* (1996) 55: 437-441.
Easty, et al., "Abnormal protein tyrosine kinase gene expression during melanoma progression and metastasis" *Int. J. Cancer* (1995) 60: 129-136.
Easty, et al., "Cytokine B61 as a growth factor for metastatic melanomas and increasing expression of its receptor Eck during melanoma progression" *Proc. Am. Asso. Cancer Mtng.* (1994) vol. 35 (Abstract; 85th Annual Meeting, American Association for Cancer Research, San Francisco, CA, Apr. 10-13, 1994).
Easty, et al., "Protein B61 as a new growth factor: expression of B61 and up-regulation of its receptor epithelial cell kinase during melanoma progression" *Cancer Res.* (1995) 55: 2528-2532.
Eberhart, et al., "EphA4 constitutes a population-specific guidance cue for motor neurons" *Dev. Biol.* (2002) 247: 89-101.
Ellerby, et al., "Anti-cancer activity of targeted pro-apoptotic peptides" *Nat. Med.* (1999) 5(9): 1032-1038.
Ellis, et al., "Embryo brain kinase: a novle gene of the eph/elk receptors tyrosine kinase family" *Mechanisms Devel.* (1995) 52: 319-341.
Essler, et al., "Molecular specialization of breast vasculature: a breast-homing phage-displayed peptide binds to aminopeptidase P In breast vasulature" *PNAS USA* (2002) 99: 2252-2257.
Fairbrother, et al., "Novel peptides selected to bind vascular endothelial growth factor target the receptor-binding site" *Biochemistry* (1998) 37(51): 17754-17764.

Fang, et al., "A kinase-dependent role for EphA2 receptor in promoting tumor growth and metastasis" *Oncogene* (2005) 24: 7859-7868.
Flanagan, et al., "The ephrins and Eph receptors in neural development" *Auun. Rev. Neurosci.* (1998) 21: 309-345.
Fumoleau, et al., "Docetaxel: a new active agent in the therapy of metastatic breast cancer" *Expert Opin. Investig. Drugs* (1997) 6: 1853-1865 (Abstract Only).
Gale, et al., "Eph Receptors and Ligands Comprise Two Major Specificity Subclasses and Are Reciprocally Compartmentalized during Embryogenesis" *Neuron* (1996) 17(1): 9-19.
Ganju, et al., "The Eck receptor tyrosine kinase is implicated in pattern formation during gastrulation, hindbrain segmentation and limb development" *Oncogene* (1994) 9: 1613-1624.
Gerlag, et al., "Suppression of murine collagen-induced arthritis by targeted apoptosis of synovial neovasculature" *Arthritis Res.* (2001) 3(6): 357-361.
Goldshmit, et al., "Axonal regeneration and lack of astrocytic gliosis in EphA4-deficient mice" *J. Neurosci.* (2004) 24(45): 10064-10073.
Hafner, et al., "Differential gene expression of Eph receptors and ephrins in benign human tissues and cancers" *Clin. Chem.* (2004) 50(3): 490-499.
Hajduk, et al., "Discovering High-Affinity Ligands for Protein" *Science* (1997) 278(5337): 497-499.
Hess, et al., "Molecular regulation of tumor cell vasculogenic mimicry by tyrosine phosphorylation: role of epithelial cell kinase (Eck/EphA2)" *Cancer Res.* (2001) 61: 3250-3255.
Hill, et al., "Phage presentation" *Mol. Microniol.* (1996) 20: 685-692 (Abstract Only).
Himanen, et al., "Crystal structure of the ligand-binding domain of the receptor tyrosine kinase EphB2" *Nature* (1998) 396(6710): 486-491.
Himanen, et al., "Crystal structure of an Eph receptor-ephrin complex" *Nature* (2001) 414(6866): 933-938.
Himanen, et al., "Repelling class discrimination: ephrin-A5 binds to and activates EphB2 receptor signaling" *Nat. Neurosci.* (2004) 7(5): 501-509.
Holash, et al., "Polarized expression of the receptor protein tyrosine kinase Cek5 in the developing avian visual system" *Dev. Biol.* (1995) 172(2): 683-693.
Hu, et al., "Genome-wide association study in esophageal cancer using GeneChip mapping 10K array" *Cancer Res.* (2005) 65(7): 2542-2546.
Koivunen, et al., "Isolation of a highly specific ligand for the alpha$_5$beta$_1$ integrin from a phage display library" *J. Cell Biol.* (1994) 124: 373-380.
Koivunen, et al., "Tumor targeting with a selective geletinase inhibitor" *Nat. Biotechnol.* (1999) 17: 768-774.
Koolpe, et al., "An ephrin mimetic peptide that selectively targets the EphA2 receptor" *J. Biol. Chem.* (2002) 277(49): 46974-46979.
Koolpe, et al., "EphB receptor-binding peptides identified by phage display enable design of an antagonist with ephrin-like affinity" *J. Biol. Chem.* (2005) 280(17): 17301-17311.
Kozlosky, et al., "Ligands for the receptor tyrosine kinases hek and elk: isolation of cDNAs encoding a family of proteins" *Oncogene* (1995) 10: 299-306.
Kropinski, 2000, NCBI Accession No. NP_061584, p. 1. [retrieved on Jul. 18, 2008]. Retrieved from the Internet: <http://www.ncbi.nlm.gov/entrez/viewer.fcgi?9635674:OLD04:08244>.
Kullander, et al., "Mechanisms and functions of Eph and ephrin signaling" *Nat. Rev. Mol. Cell. Biol.* (2002) 3(7): 475-486.
Kuntz, "Structure-based strategies for drug design and discovery" *Science* (1992) 257(5073): 1078-1082.
Labrador, et al., "The N-terminal globular domain of Eph receptors is sufficient for ligand binding and receptor signaling" *EMBO J.* (1997) 16: 3889-3897.
Lackmann, et al., "Distinct subdomains of the EphA3 receptor mediate ligand binding and receptor dimerization" *J. Biol. Chem.* (1998) 273(32): 20228-20237.
Lackmann, et al., "Ligand for EPH-related kinase (LERK) 7 is the preferred high affinity ligand for the HEK receptor" *J. Biol. Chem.* (1997) 272(26): 16521-16530.
Lin et al., "The carboxyl terminus of B class ephrins constitutes a PDZ domain binding motif" *J. Biol. Chem.* (1999) 274(6): 3726-3733.

Livnah, et al., "Functional mimicry of a protein hormone by a peptide agonist: the EPO receptor complex at 2.8 A" *Science* (1996) 273(5274): 464-471.

Lowman, et al., "Molecular mimics of insulin-like growth factor 1 (IGF-1) for inhibiting IGF-1: IGF-binding protein interactions" *Biochem.* (1998) 37(25): 8870-8878.

Magal, et al., "B61, a ligand for the Eck receptor protein-tyrosine kinase, exhibits neurotrophic activity in cultures of rat spinal cord neurons" *J. Neuroscience Res.* (1996) 43: 735-744.

Manning, et al., "Evolution of protein kinase signaling from yeast to man" *Trends Biochem Sci.* (2002) 27: 514-520.

McBride, et al., "Ephrin-A1 is expressed at sites of vascular development in the mouse" *Mech. Dev.* (1998) 77: 201-204.

McLeannan, et al., "Ephrin-As cooperate with EphA4 to promote trunk neural crest migration" *Gene Expression* (2002) 10: 295-305.

Meima, et al., "Lerk2 (Ephrin-B1) is a collapsing factor for a subset of cortical growth cones and acts by a mechanism different from AL-1 (Ephrin-A5)" *Molecular and Cellular Neuroscience* (1997) 9: 314-328.

Miao, et al., "Activation of EphA2 kinase suppresses integrin function and causes focal-adhesion-kinase dephosphorylation" *Nat. Cell. Biol.* (2000) 2(2): 62-69.

Miao, et al., "Activation of EphA receptor tyrosine kinase inhibits the Ras/MAPK pathway" *Nature Cell Biol.* (2001) 3: 527-530.

Miller, et al., "Ligand binding to proteins: the binding landscape model" *Protein Sci.* (1997) 6(10): 2166-2179.

Miranda, et al., "Induction of Eph B3 after spinal cord injury" *Exp. Neurol.* (1999) 156: 218-222.

Moore, et al., "Morphogenetic movements underlying eye field formation require interactions between the FGF and ephrinB1 signaling pathways" *Dev. Cell.* (2004) 6(1): 55-67.

Mori, et al., "Differential expressions of the eph family of receptor tyrosine kinase genes (sek, elk, eck) in the developing nervous system of the mouse" *Mol. Brain Res.* (1995) 29: 325-335.

Mori, et al., "Localization of novel receptor tyrosine kinase genes of the eph family, MDK1 and its splicing variant, in the developing mouse nervous system" *Mol. Brain Res.* (1995) 34: 154-160.

Murai, et al., "Control of hippocampal dendritic spine morphology through ephrinA3/EphA4 signaling" *Nat. Neurosci* (2003) 6: 153-160.

Murai, et al., "Eph'ective signaling: forward, reverse and crosstalk" *J. Cell Sci.* (2003) 116(Pt. 14): 2823-2832.

Murai, et al., "Targeting the EphA4 receptor in the nervous system with biologically active peptides" *Mol. Cell Neurosci* (2003) 24(4): 1000-1011.

Myers, et al., "Homebox B3 promotes capillary morphogenesis and angiogensis" *J. Cell Biol.* (2000) 148: 343-351.

Nakamoto, et al., "Diverse roles for the Eph family of receptor tyrosine kinases in carcinogenesis" *Microsc. Res. Tech.* (2002) 59(1): 58-67.

Neidigh, et al., "Designing a 20-residue protein" *Nat. Struct. Biol.* (2002) 9(6): 425-430.

Nemoto, et al., "Overexpression of protein tyrosine kinases in human esophageal cancer" *Pathobiology* (1997) 65: 195-203.

Nieto, et al., "A receptor protein tyrosine kinase implicated in the segmental patterning of the hindbrain and mesoderm" *Development* (1992) 116: 1137-1150.

Nikolova, et al., "Cell-type specific and estrogen dependent expression of the receptor tyrosine kinase EphB4 and its ligand ephrin-B2 during mammary gland morphogensis" *J. Cell Sci.* (1998) 111: 2741-2751.

Noren, et al., "Interplay between EphB4 on tumor cells and vascular ephrin-B2 regulates tumor growth" *PNAS USA* (2004) 101(15): 5583-5588.

Noren, et al., "Paradoxes of the EphB4 Receptor in Cancer" *Cancer Res.* (2007) 67(9): 3994-3997.

Ogawa, et al., "The ephrin-A1 ligand and its receptor, EphA2, are expressed during tumor neovascularization" *Oncogene* (2000) 19(52): 6043-6052.

Ogawa, et al., "EphB2 and ephrin-B1 expressed in the adult kidney regulate the cytoarchitecture of medullary tubule cells through Rho family GTPases" *J. Cell Sci.* (2006) 119(Pt. 3): 559-570.

Ohta, et al., "The receptor tyrosine kinase, Cek8 is transiently expressed on subtypes of motoneurons in the spinal cord during development" *Mech. Devel.* (1996) 54: 59-69.

Olivieri, et al., "Immunohistochemical localization of EphA5 in the adult human central nervous system" *J. Histochem. Cytochem.* (1999) 47: 855-861.

Pandey, et al., "Role of B61, the ligand for the Eck receptor tyrosine kinase, in TNF—induced angiogenesis" *Science* (1995) 268: 567-569.

Prevost, et al., "Eph kinases and ephrins support thrombus growth and stability by regulating integrin outside-in signaling in platelets" *PNAS USA* (2005) 102(28): 9820-9825.

Prevost, et al., "Interactions between Eph kinases and ephrins provide a mechanism to support platelet aggregation once cell-to-cell contact has occurred" *PNAS USA* (2002) 99: 9219-9224.

Rivkin, et al., "Molecular cloning of rat sperm galactosyl receptor, a C-type lectin with in vitro egg binding activity" *Mol. Reprod. Dev.* (2000) 56: 401-411.

Rogers, et al., "Structure-activity relationships in a peptidic alpha7 nicotinic acetylcholine receptor antagonist" *J. Mol. Biol.* (2000) 304: 911-926.

Ruiz, et al., "The expression of the receptor-protein tyrosine kinase gene, eck, is highly restricted during early mouse development" *Mech. Dev.* (1994) 46: 87-100.

Salvucci, et al., "EphB2 and EphB4 receptors forward signaling promotes SDF-1-induced endothelial cell chemotaxis and branching remodeling" *Blood* (2006) 108(9): 2914-2922.

Skolnick, et al., "From genes to protein structure and function: novel applications of computational approaches in the genomic era" *Trends in Biotech* (2000) 18(1): 34-39.

Smith, et al., "Dissecting the EphA3/Ephrin-A5 interactions using a novel functional mutagenesis screen" *J. Biol. Chem.* (2004) 279(10): 9522-9531.

Smith, et al., The challenges of genome sequence annotation or "the devil is the in the details" *Nature Biotech* (1997) 15: 1222-1223.

Smith, "Filamentous fusion phage: novel expression vectors that display cloned antigens on the virion surface" *Science* (1985) 228: 1315-1317.

Soans, et al., "Characterization of the expression of the Cek8 receptor-type tyrosine kinase during development and in tumor cell lines" *Oncogene* (1994) 9: 3353-3361.

Song, et al., "Solution structure and backbone dynamics of the functional cytoplasmic subdomain of human ephrin B2, a cell-surface ligand with bidirectional signaling properties" *Biochemistry* (2002) 41(36): 10942-10949.

Stein, et al., "Eph receptors discriminate specific ligand oligomers to determine alternative signaling complexes, attachment, and assembly responses" *Genes Dev.* (1998) 12: 667-678.

Sturz, et al., "EphB4 signaling is capable of mediating ephrinB2-induced inhibition of cell migration" *Biochem. Biophys. Res. Comm.* (2004) 313: 80-88.

Surawska, et al., "The role of ephrins and Eph receptors in cancer" *Cytokine & Growth Factor Reviews* (2004) 15: 419-433.

Thompson, "Ephrins keep dendritic spines in shape" *Nature Neuroscience* (2003) 6: 103-104.

Toth, et al., "Crystal structure of an ephrin ectodomain" *Dev. Cell* (2001) 1: 83-92.

Twigg, et al., "Mutations of ephrin-B1 (EFNB1), a marker of tissue boundary formation, cause craniofrontonasal syndrome" *PNAS USA* (2004) 101(23): 8652-8657.

Van Der Greer, et al., "Receptor Protein-Tyrosine Kinases and their Signal Transduction Pathways" *Annu. Rev. Cell Biol.* (1994) 10: 251-337.

Walker-Daniels, et al., "Differential regulation of EphA2 in normal and malignant cells" *Am. J. Pathol.* (2003) 162(4): 1037-1042.

Walker-Daniels, et al., "Overexpression of the EphA2 tyrosine kinase in prostate cancer" *Prostate* (1999) 41: 275-280.

Wang, et al., "Molecular distinction and angiogenic interaction between embryonic arteries and veins revealed by ephrin-B2 and its receptor Eph-B4" *Cell* (1998) 93: 741-753.

Wang, et al., "Molecular distinction and angiogenic interactions between embryonic arteries and veins revealed by EphrinB2 and its receptor EphB4" Abstracts from 71$^{st}$ Scientific Sessions, Nov. 8-11, 1998, Callas, Texas; *Circulation*, 98(17): Abstract 341.

Wieland, et al., "Mutations of the ephrin-B1 gene cause craniofrontonasal syndrome" *Am. J. Hum. Genet.* (2004) 74(6): 1209-1215.

Willson, et al., "Upregulation of EphA receptor expression in the injured adult rat spinal cord" *Cell Transplantation* (2002) 11: 229-239.

Wrighton, et al., "Small peptides as potent mimetics of the protein hormone erythropoietin" *Science* (1996) 273(5274): 458-464.

Yancopoulos, et al., "Vasculogensis, Angiogensis, and growth factors: ephrins enter the fray at the border" *Cell* (1998) 93: 661-664.

Yancopoulos, et al., "Vascular-specific growth factors and blood vessel formation" *Nature* (2000) 407: 242-248.

Yue, et al., "Specification of distinct dopaminergic neural pathways: roles of the Eph family receptor EphB1 and ligand Ephrin-B2" *J. Neurosci.* (1999) 19: 2090-2101.

Zantek, et al., "E-cadherin regulates the function of the EphA2 receptor tyrosine kinase" *Cell Growth Differ.* (1999) 10(9): 629-638.

Zelinski, et al., "EphA2 overexpression causes tumorigensis of mammary epithelial cells" *Cancer Res.* (2001) 61: 2301-2306.

Zelinski, et al., "Estrogen and Myc negatively regulate expression of the EphA2 tyrosine kinase" *J. Cell. Biochem.* (2002) 85(4): 714-720.

Zhang, et al., "Dynamic expression suggests multiple roles of the eph family receptor brain-specific kinase (Bsk) during mouse neurogenesis" *Mol. Brain Res.* (1997) 47: 202-214.

Zhou, "The Eph family receptors and ligands" *Pharmacol. Ther.* (1998) 77(3): 151-181.

Dictionary definition of ligand. 1 page. [retrieved on Jul. 18, 2005]. Retrieved from the Internet: <http://dictionary.reference.com/search?q=ligand>.

Eph Nomenclature Committee, "Unified nomenclature for Eph family receptors and their ligands, the ephrins" *Cell* (1997) 90: 403-404.

NCBI Accession No. P20761 (GI: 121055). "Ig gamma-2B chain C region" NCBI Database. 2 pages. [retrieved on Jul. 18, 2005]. Retrieved from the Internet: <http://www.ncbi.nlm.nih.gov/entrez/viewer.fcgi?db=protein&val=121055>.

Supplementary Partial European Search Report from European Patent Application No. EP03749303, Nov. 22, 2005.

* cited by examiner

US 7,999,069 B2

EPHB RECEPTOR-BINDING PEPTIDES

CROSS-REFERENCE TO RELATED APPLICATIONS

This application is a continuation of U.S. Ser. No. 11/342, 247, filed Jan. 26, 2006, which claims priority and the benefit under 35 U.S.C. §119 (e) of U.S. Provisional Application No. 60/462,024 filed Jan. 27, 2005, which disclosures are herein incorporated by reference.

GOVERNMENTAL INTERESTS

This invention was made with government support under grant numbers CA82713 and HD25938 awarded by the National Institutes of Health and a grant number DAMD17-01-1-0168 awarded by the Department of Defense. The United States Government has certain rights in this invention.

REFERENCE TO A SEQUENCE LISTING

This application incorporates by reference the Sequence Listing submitted with parent application Ser. No. 11/342, 247 filed Jan. 26, 2006.

FIELD OF THE INVENTION

The application is related to antagonistic peptides that selectively bind to Eph receptors of the B class, including EphB1, EphB2, and EphB4. Also included are methods for identifying such peptides.

DESCRIPTION OF THE RELATED ART

The Eph receptors are a large family of receptor tyrosine kinases that regulate a multitude of biological processes in developing, as well as adult, tissues by binding a family of ligands called ephrins (Murai, K. K., & Pasquale, E. B. 2003 *J Cell Sci* 116:2823-2832). The Eph receptors are differentially expressed in a variety of healthy tissues (Hafner, C. et al. 2004 *Clinical Chem* 50:490-499) and have been implicated in a variety of aspects of normal functions, such as pain processing (Battaglia, A. A. et al. 2003 *Nat Neurosci* 6:339-340), platelet aggregation, neuronal development, cell migration and adhesion (Prevost, N. et al. 2005 *PNAS USA* 102:9820-9825). The Eph receptors have also been implicated in a variety of pathological processes, including tumor progression (Dodelet, V. C., & Pasquale, E. B. 2000 *Oncogene* 19:5614-5619; Nakamoto, M. & Bergemann, A. D. 2002 *Microsc Res Tech* 59:58-67; Walker-Daniels, J. et al. 2003 *Am J Pathol* 162:1037-1042; Hu, N. et al. 2005 *Cancer Res* 65:2542-2546; Hafner, C. et al. 2004 *Clin Chem* 50:490-499), pathological forms of angiogenesis (Adams, R. H., & Klein, R. 2000 *Trends Cardiov Medicine* 10:183-188; Brantley-Sieders, D. M., & Chen, J. 2004 *Angiogenesis* 7:17-28; Noren, N. K. et al. 2004 *PNAS USA* 101:5583-5588), chronic pain following tissue damage (Battaglia, A. A. et al. 2003 *Nat Neurosci* 6:339-340), inhibition of nerve regeneration after spinal cord injury (Goldshmit, Y. et al. 2004 *J Neurosci* 24:10064-10073), and human congenital malformations (Twigg, S. R. et al. 2004 *PNAS USA* 101:8652-8657; Wieland, I. et al. 2004 *Am J Hum Genet.* 74:1209-1215). Furthermore, these receptors have been reported to play a role in the balance of stem cell self-renewal versus cell-fate determination and differentiation (Conover, J. C. et al. 2000 *Nat Neurosci* 3:1091-1097; Aoki, M. et al. 2004 *J Biol Chem* 279:32643-32650; Moore, K. B. et al. 2004 *Dev Cell* 6:55-67).

The ephrin ligands can discriminate between the EphA and EphB classes of receptors. Ephrin-A ligands bind to EphA receptors, with the exception of ephrin-A5 which at high concentrations can bind to EphB2 (Himanen, J. P. et al. 2004 *Nat Neurosci* 7:501-509). Ephrin-B ligands bind to EphB receptors as well as EphA4 (Gale, N. W. et al. 1996 *Neuron* 17:9-19; Kullander, K. & Klein, R. 2002 *Nat Rev Mol Cell Biol* 3:475-486). However, interactions between Eph receptors and ephrins belonging to the same class are highly promiscuous (Murai, K. K., & Pasquale, E. B. 2003 *J Cell Sci* 116:2823-2832; Kullander, K. & Klein, R. 2002 *Nat Rev Mol Cell Biol* 3:475-486; Flanagan, J. G. & Vanderhaeghen, P. 1998 *Annu Rev Neurosci* 21:309-345). Nevertheless, several 12 amino acid-long peptides identified by phage display bind selectively to one or few Eph receptors of the A class (Koolpe, M. et al. 2002 *J Biol Chem* 277:46974-46979; Murai, K. K. et al. 2003 *Mol Cell Neurosci* 24:1000-1011). These peptides have some sequence similarity with the 15 amino acid-long G-H loop of the ephrins, which is the main region mediating high affinity binding of the ephrins to the Eph receptors (Himanen, J. P et al. 2001 *Nature* 414:933-938). In particular, several of the EphA receptor-binding peptides contain the motif ΦxxΦ (where "x" is a non-conserved amino acid and Φ is an aromatic amino acid (Aasland, R. et al. 2002 *FEBS Lett* 513:141-144)), which is also found in the G-H loop of A-class ephrins. These peptides have additional distinctive sequence features that presumably confer their binding selectivity for specific EphA receptors. Micromolar concentrations of peptides that bind to EphA2 and EphA4 inhibit ephrin binding to these receptors (Koolpe, M. et al. 2002 *J Biol Chem* 277: 46974-46979; Murai, K. K. et al. 2003 *Mol Cell Neurosci* 24:1000-1011). Additionally, the EphA4-binding peptides are antagonists that inhibit receptor activation by ephrins (Murai, K. K. et al. 2003 *Mol Cell Neurosci* 24:1000-1011), whereas the EphA2-binding peptides behave as ephrin mimics and promote EphA2 activation and downstream signaling (Koolpe, M. et al. 2002 *J Biol Chem* 277:46974-46979). The antagonistic peptides likely function by preventing ephrin-dependent Eph receptor clustering and transphosphorylation, which are necessary steps to activate downstream signaling pathways (Murai, K. K., & Pasquale, E. B. 2003 *J Cell Sci* 116:2823-2832). In fact, the cell surface-anchored ephrins promote the formation of Eph receptor dimers as well as larger clusters in which the receptors become activated (Himanen, J. P et al. 2001 *Nature* 414:933-938), but soluble monomeric forms of the ephrins act as antagonists (Davis, S. et al. 1994 *Science* 266:816-819). In contrast, it is currently unclear how the EphA2-binding peptides can activate EphA2.

SUMMARY OF THE INVENTION

One embodiment of the present invention is a peptide which selectively binds to a member of the EphB receptor family and inhibits binding of Ephrin-B to a member of the EphB receptor family.

Another embodiment of the present invention is an isolated peptide which mimics an ephrin G-H loop and selectively binds to a member of the EphB receptor family and inhibits binding of Ephrin-B to a member of the EphB receptor family.

Another embodiment of the present invention is an isolated peptide selected from the group of peptides of SEQ ID NOs: 1-39. In one embodiment of the present invention, the isolated peptide has a sequence of SEQ ID NO: 1. In another embodiment of the present invention, the isolated peptide has a sequence of SEQ ID NO: 2. In another embodiment of the present invention, the isolated peptide has a sequence of SEQ ID NO: 3. In another embodiment of the present invention, the isolated peptide has a sequence of SEQ ID NO: 4. In another embodiment of the present invention, the isolated peptide has a sequence of SEQ ID NO: 5. In another embodiment of the present invention, the isolated peptide has a sequence of SEQ ID NO: 39.

Another embodiment of the present invention is the peptide which selectively binds to a member of the EphB receptor family and inhibits binding of Ephrin-B to a member of the EphB receptor family is in composition with a pharmaceutically acceptable carrier.

Another embodiment of the present invention is a method for treating an EphB receptor related disease in a patient by identifying a patient in need for such treatment and administering to the patient a therapeutically effective amount of the isolated peptide which selectively binds to a member of the EphB receptor family and inhibits binding of Ephrin-B to a member of the EphB receptor family is in composition with a pharmaceutically acceptable carrier. Such EphB receptor related disease may be a neoplastic disease, a neurological disease or a vascular disease. In another embodiment, the peptide is linked to a chemotherapeutic drug or toxin.

Another embodiment of the present invention is a method of imaging a tumor in a patient by identifying a patient suspected of having a tumor that expresses an EphB receptor and administering to the patient an isolated peptide which selectively binds to a member of the EphB receptor family and inhibits binding of Ephrin-B to a member of the EphB receptor family, while the peptide is linked to an imaging agent, and obtaining an image of the imaging agent in the patient. In one embodiment, the imaging agent is fluorescent. In another embodiment, the imaging agent is radioactive.

DETAILED DESCRIPTION OF THE PREFERRED EMBODIMENT

Figure 1:
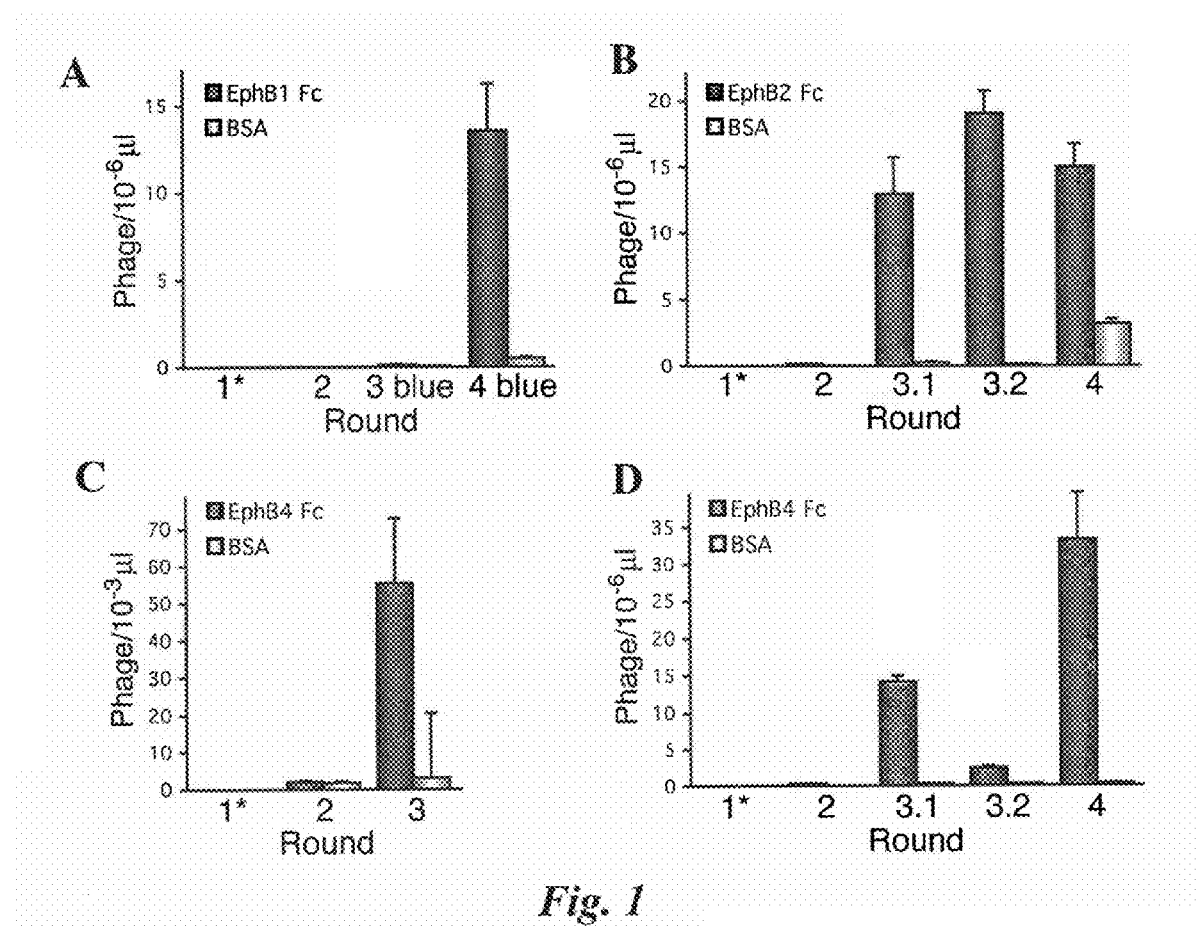
FIGS. 1A-D are bar graphs showing enrichment of phage clones that bind to EphB receptors. (A) Enrichment using EphB1 panning. (B) Enrichment using EphB2 panning. (C and D) Enrichment using EphB4 panning.

The Eph receptor tyrosine kinases are overexpressed in many pathologic tissues and have therefore emerged as promising drug target candidates. However, there are few molecules available that can selectively bind to a single Eph receptor and not other members of this large receptor family. One embodiment of the invention relates to peptides that bind selectively to different receptors of the EphB class, including EphB1, EphB2, Eph B3 and EphB4. Peptides with the same EphB receptor specificity were found to compete with each other for binding, suggesting that they have partially overlapping binding sites. In addition, several of the peptides contain amino acid motifs found in the G-H loop of the ephrin-B ligands, which is the region that mediates high-affinity interaction with the EphB receptors. Consistent with targeting the ephrin-binding site, the higher-affinity peptides antagonize ephrin binding to the EphB receptors.

Both EphB2 and EphB4 are overexpressed in a wide variety of cancers and peptides that bind to these receptors would thus be useful for imaging and drug targeting applications. As described below, some peptides, such as TNYL, effectively delivered fluorescent quantum dots to EphB4-expressing cells. There are also many possible uses for EphB receptor antagonists, particularly in cancer therapy. For example, the interplay between EphB4 expressed in breast cancer cells and ephrin-B2 expressed in the tumor vasculature was reported wherein the cytoplasmic domain of the transmembrane ephrin-B2 ligand promoted tumor growth by stimulating angiogenesis (Noren, N. K. et al. 2004 *PNAS USA* 101:5583-5588).

Thus, the TNYL-RAW peptide could be developed to inhibit tumor progression and other forms of pathological angiogenesis that may similarly depend on EphB4 and ephrin-B2. Combinations of peptides that bind to EphA and EphB class receptors involved in a particular pathological process, such as EphB4 and EphA2 in cancer are also envisioned. Finally, the affinity of the EphB receptor binding peptides may be greatly increased by dimerization through a flexible linker. However, it is possible that the dimerized peptides may become agonists.

As discussed below, embodiments of the invention relate to the use of Eph receptor binding ligands as treatments Eph receptor related diseases. Examples of such diseases include neoplastic diseases, neurological diseases, and vascular diseases. In some embodiments, the Eph receptor related disease includes Eph B1 receptor related diseases. An Eph B1 related disease includes those diseases associated with higher than normal expression of the Eph B1 receptor. Accordingly, binding ligands targeting the Eph B1 receptor would have therapeutic effectiveness against such Eph BI receptor related diseases. Examples of Eph B1 receptor related diseases includes neoplastic diseases, neurological diseases, and vascular diseases.

DEFINITIONS

The following definitions are set forth to illustrate and define the meaning and scope of the various terms used to describe the invention herein.

As used herein, "agonist" refers to a biologically active ligand which binds to its complementary biologically active receptor and activates the latter either to cause a biological response in the receptor or to enhance preexisting biological activity of the receptor.

As used herein, "antagonist" refers to a biologically active ligand which binds to its complementary biologically active receptor and inhibits the physiological response of the receptor.

As used herein, "pharmaceutically acceptable salts" refer to the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like.

As used herein, "pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. For a description of pharmaceutically acceptable acid addition salts as prodrugs, see Bundgaard, H. ed. 1985 *Design of Prodrugs*, Elsevier Science Publishers, Amsterdam.

As used herein, "pharmaceutically acceptable ester" refers to those esters which retain, upon hydrolysis of the ester bond, the biological effectiveness and properties of the carboxylic acid or alcohol and are not biologically or otherwise undesirable. For a description of pharmaceutically acceptable esters as prodrugs, see Bundgaard, H. ed. 1985 *Design of Prodrugs*, Elsevier Science Publishers, Amsterdam. These esters are typically formed from the corresponding carboxylic acid and an alcohol. Generally, ester formation can be accomplished via conventional synthetic techniques. See, for example, March, 1992 *Advanced Organic Chemistry*, 4th Ed., John Wiley & Sons, New York, p.p. 393-396 and references cited therein, and Mark, et al. 1980 *Encyclopedia of Chemical Technology*, John Wiley & Sons, New York. The alcohol component of the ester will generally comprise (i) a $C_2$-$C_{12}$ aliphatic alcohol that can or can not contain one or more double bonds and can or can not contain branched carbons or (ii) a $C_7$-$C_{12}$ aromatic or heteroaromatic alcohols. This invention also contemplates the use of those compositions which are both esters as described herein and at the same time are the pharmaceutically acceptable acid addition salts thereof.

As used herein, "pharmaceutically acceptable amide" refers to those amides which retain, upon hydrolysis of the amide bond, the biological effectiveness and properties of the carboxylic acid or amine and are not biologically or otherwise undesirable. For a description of pharmaceutically acceptable amides as prodrugs, see Bundgaard, H. ed. 1985 *Design of Prodrugs* Elsevier Science Publishers, Amsterdam. These amides are typically formed from the corresponding carboxylic acid and an amine. Generally, amide formation can be accomplished via conventional synthetic techniques. See, for example, March, 1992 *Advanced Organic Chemistry*, 4th Ed., John Wiley & Sons, New York, p. 393 and Mark, et al. 1980 *Encyclopedia of Chemical Technology*, John Wiley & Sons, New York. This invention also contemplates the use of those compositions which are both amides as described herein and at the same time are the pharmaceutically acceptable acid addition salts thereof.

As used herein, "pharmaceutically or therapeutically acceptable carrier" refers to a carrier medium which does not interfere with the effectiveness of the biological activity of the active ingredients and which is not toxic to the host or patient.

As used herein, "stereoisomer" refers to a chemical compound having the same molecular weight, chemical composition, and bonding sequence as another, but having its atoms grouped differently in space about one or more chiral centers. That is, stereoisomers of the same chemical formula will contain identical chemical moieties located in different spacial orientations about at least one chiral center. When pure, stereoisomers have the ability to rotate plane-polarized light. Some pure stereoisomers, however, may have an optical rotation that is so slight that it is undetectable with present instrumentation. The compounds of the instant invention may have one or more asymmetrical carbon atoms and therefore include various stereoisomers. All stereoisomers are included within the scope of the invention.

As used herein, "therapeutically- or pharmaceutically-effective amount" as applied to the compositions of the instant invention refers to the amount of composition sufficient to induce a desired biological result. That result can be alleviation of the signs, symptoms, or causes of a disease, or any other desired alteration of a biological system. In the present invention, the result will, for example, involve inhibition and/or reversal of cancerous cell growth.

As used herein, the terms "peptide compound" and "peptidic structure" are intended to include peptides comprised of naturally-occurring L-amino acids, as well as peptide derivatives, peptide analogues and peptidomimetics of the naturally-occurring L-amino acid structures. The terms "peptide analogue", "peptide derivative" and "peptidomimetic" as used herein are intended to include molecules which mimic the chemical structure of a peptide and retain the functional properties of the peptide. Approaches to designing peptide analogues, derivatives and mimetics are known in the art. For example, see Farmer, P. S. in: *Drug Design* E. J. Ariens, ed. Academic Press, New York, 1980, vol. 10, pp. 119-143; Ball J. B. & Alewood, P. F. 1990 *J Mol Recognition* 3:55; Morgan, B. A. & Gainor, J. A. 1989 *Ann Rep Med Chem* 24:243; and Freidinger, R. M. 1989 *Trends Pharmacol Sci* 10:270; Luthman, et al. 1996 *A Textbook of Drug Design and Development,* 14:386-406, 2nd Ed., Harwood Academic Publishers; Joachim Grante, Angew. 1994 *Chem Int Ed Engl* 33:1699-1720; Fauchere, J. 1986 *Adv Drug Res* 15:29; Veber and Freidinger 1985 *TINS* p. 392; Evans, et al. 1987 *J Med Chem* 30:229, all of which are hereby incorporated by reference. Peptidomimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as naturally-occurring receptor-binding polypeptide, but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —$CH(OH)CH_2$—, and —$CH_2SO$—, by methods known in the art and further described in the following references: Spatola, A. F. 1983 in: *Chemistry and Biochemistry of Amino Acids, Peptides, and Proteins,* B. Weinstein, eds., Marcel Dekker, New York, p. 267; Spatola, A. F. 1983 *Vega Data,* Vol. 1, Issue 3, *Peptide Backbone Modifications* (general review); Morley, 1980 *Trends Pharm Sci* pp. 463-468, (general review); Hudson, et al. 1979 *Int J Pept Prot Res* 14:177-185 (—$CH_2NH$—, $CH_2CH_2$—); Spatola, et al. 1986 *Life Sci* 38:1243-1249 (—$CH_2$—S); Hann, 1982 *J Chem Soc Perkin Trans I* 307-314 (—CH—CH—, cis and trans); Almquist, et al. 1980 *J Med Chem* 23:1392-1398, (—$COCH_2$—); Jennings-White, et al. 1982 *Tetrahedron Len* 23:2533 (—$COCH_2$—); Szelke, et al. 1982 European Appln. EP 45665 (—$CH(OH)CH_2$—); Holladay, et al. 1983 *Tetrahedron Lett* 24:4401-4404 (—C(OH) $CH_2$—); and Hruby, 1982 *Life Sci* 31:189-199 (—$CH_2$—S—); each of which is incorporated herein by reference. Such peptidomimetics may have significant advantages over polypeptide embodiments, including, for example: more economical production, greater chemical stability, enhanced pharmacological properties (half-life, absorption, potency, efficacy, etc.), altered specificity (for example, a broad-spectrum of biological activities), reduced antigenicity, and others. Labeling of peptidomimetics usually involves covalent attachment of one or more labels, directly or through a spacer (for example, an amide group), to non-interfering position(s) on the peptidomimetic that are predicted by quantitative structure-activity data and/or molecular modeling. Such non-interfering positions generally are positions that do not form direct contacts with the macromolecules(s) (such as, receptor molecules) to which the peptidomimetic binds to produce the therapeutic effect. Derivatization (for example, labeling) of peptidomimetics should not substantially interfere with the desired biological or pharmacological activity of the peptidomimetic. Generally, peptidomimetics of receptor-binding peptides bind to the receptor with high affinity and possess detectable biological activity (i.e., are agonistic or antagonistic to one or more receptor-mediated phenotypic changes).

Systematic substitution of one or more amino acids of a consensus sequence with a D-amino acid of the same type (for example, D-lysine in place of L-lysine) may be used to generate more stable peptides. In addition, constrained peptides comprising a consensus sequence or a substantially identical consensus sequence variation may be generated by methods known in the art (Rizo, et al. 1992 *Ann Rev Biochem* 61:387, incorporated herein by reference); for example, by adding internal cysteine residues capable of forming intramolecular disulfide bridges which cyclize the peptide.

Synthetic or non-naturally occurring amino acids refer to amino acids which do not naturally occur in vivo but which, nevertheless, can be incorporated into the peptide structures described herein. Preferred synthetic amino acids are the D-α-amino acids of naturally occurring L-α-amino acid as well as non-naturally occurring D- and L-α-amino acids represented by the formula $H_2NCHR^5COOH$ where $R^5$ is 1) a lower alkyl group, 2) a cycloalkyl group of from 3 to 7 carbon atoms, 3) a heterocycle of from 3 to 7 carbon atoms and 1 to 2 heteroatoms selected from the group consisting of oxygen, sulfur, and nitrogen, 4) an aromatic residue of from 6 to 10 carbon atoms optionally having from 1 to 3 substituents on the aromatic nucleus selected from the group consisting of hydroxyl, lower alkoxy, amino, and carboxyl, 5)-alkylene-Y where alkylene is an alkylene group of from 1 to 7 carbon atoms and Y is selected from the group consisting of (a) hydroxy, (b) amino, (c) cycloalkyl and cycloalkenyl of from 3 to 7 carbon atoms, (d) aryl of from 6 to 10 carbon atoms optionally having from 1 to 3 substituents on the aromatic nucleus selected from the group consisting of hydroxyl, lower alkoxy, amino and carboxyl, (e) heterocyclic of from 3 to 7 carbon atoms and 1 to 2 heteroatoms selected from the group consisting of oxygen, sulfur, and nitrogen, (f) —$C(O)R^2$ where $R^2$ is selected from the group consisting of hydrogen, hydroxy, lower alkyl, tower alkoxy, and —$NR^3R^4$ where $R^3$ and $R^4$ are independently selected from the group consisting of hydrogen and lower alkyl, (g) —$S(O)_nR^6$ where n is an integer from 1 to 2 and $R^6$ is lower alkyl and with the proviso that $R^5$ does not define a side chain of a naturally occurring amino acid.

Other preferred synthetic amino acids include amino acids wherein the amino group is separated from the carboxyl group by more than one carbon atom such as β-alanine, γ-aminobutyric acid, and the like.

Particularly preferred synthetic amino acids include, by way of example, the D-amino acids of naturally occurring L-amino acids, L-(1-naphthyl)-alanine, L-(2-naphthyl)-alanine, L-cyclohexylalanine, L-2-aminoisobutyric acid, the sulfoxide and sulfone derivatives of methionine (i.e., HOOC ($H_2$NCH)$CH_2CH_2S(O)_nR^6$) where n and $R^6$ are as defined above as well as the lower alkoxy derivative of methionine (i.e., HOOC—($H_2$NCH)$CH_2CH_2$—$OR^6$ where $R^6$ is as defined above).

As used herein, a "derivative" of a compound X (for example, a peptide or amino acid) refers to a form of X in which one or more reactive groups in the compound have been derivatized with a substituent group. Examples of peptide derivatives include peptides in which an amino acid side chain, the peptide backbone, or the amino- or carboxy-terminus has been substituted. As used herein an "analogue" of a compound X refers to a compound which retains chemical structures of X necessary for functional activity of X yet which also contains certain chemical structures which differ from X. An example of an analogue of a naturally occurring peptide is a peptide which includes one or more non-naturally-occurring amino acids. As used herein, a "mimetic" of a compound X refers to a compound in which chemical structures of X necessary for functional activity of X have been replaced with other chemical structures which mimic the conformation of X. Examples of peptidomimetics include peptidic compounds in which the peptide backbone is substituted with one or more benzodiazepine molecules (see for example, James, G. L. et al. 1993 *Science* 260:1937-1942), peptides in which all L-amino acids are substituted with the corresponding D-amino acids and "retro-inverso" peptides (see U.S. Pat. No. 4,522,752 by Sisto), described further below.

The term mimetic, and in particular, peptidomimetic, is intended to include isosteres. The term "isostere" as used herein is intended to include a chemical structure that can be substituted for a second chemical structure because the steric conformation of the first structure fits a binding site specific for the second structure. The term specifically includes peptide backbone modifications (i.e., amide bond mimetics) well known to those skilled in the art. Such modifications include modifications of the amide nitrogen, the α-carbon, amide carbonyl, complete replacement of the amide bond, extensions, deletions or backbone crosslinks. Several peptide backbone modifications are known, including $\phi[CH_2S]$, $\phi[CH_2NH]$, $\phi[CSNH_2]$, $\phi[NHCO]$, $\phi[COCH_2]$, and $\phi[(E)$ or $(Z) CH=CH]$. In the nomenclature used above, $\phi$ indicates the absence of an amide bond. The structure that replaces the amide group is specified within the brackets. Other examples of isosteres include peptides substituted with one or more benzodiazepine molecules (see for example, James, G. L. et al. 1993 *Science* 260:1937-1942).

Other possible modifications include an N-alkyl (or aryl) substitution ($\phi[CONR]$), backbone crosslinking to construct lactams and other cyclic structures, substitution of all D-amino acids for all L-amino acids within the compound ("inverso" compounds) or retro-inverso amino acid incorporation ($\phi[NHCO]$). By "inverso" is meant replacing L-amino acids of a sequence with D-amino acids, and by "retro-inverso" or "enantio-retro" is meant reversing the sequence of the amino acids ("retro") and replacing the L-amino acids with D-amino acids. For example, if the parent peptide is Thr-Ala-Tyr, the retro modified form is Tyr-Ala-Thr, the inverso form is thr-ala-tyr (lower case letters refer to D-amino acids), and the retro-inverso form is tyr-ala-thr. Compared to the parent peptide, a retro-inverso peptide has a reversed backbone while retaining substantially the original spatial conformation of the side chains, resulting in a retro-inverso isomer with a topology that closely resembles the parent peptide. See Goodman et al. 1981 *Perspectives in Peptide Chemistry* pp. 283-294. See also U.S. Pat. No. 4,522,752 by Sisto for further description of "retro-inverso" peptides. Other derivatives include C-terminal hydroxymethyl derivatives, O-modified derivatives (for example, C-terminal hydroxymethyl benzyl ether) and N-terminally modified derivatives including substituted amides such as alkylamides and hydrazides.

As used herein, the term "amino acid structure" (such as a "leucine structure", a "phenylalanine structure" or a "glutamine structure") is intended to include the amino acid, as well as analogues, derivatives and mimetics of the amino acid that maintain the functional activity of the compound. For example, the term "phenylalanine structure" is intended to include phenylalanine as well as pyridylalanine and homophenylalanine. The term "leucine structure" is intended to include leucine, as well as substitution with valine or other natural or non-natural amino acid having an aliphatic side chain, such as norleucine.

The amino- and/or carboxy-terminus of the peptide compounds disclosed herein can be unmodified (i.e., Y1 and/or Y2 can be, independently) hydrogen. Alternatively, the amino- and/or carboxy-terminus of the peptide compound can be modified with a derivative group. Amino-derivative groups which can be present at the N-terminus of a peptide compound (i.e., can be Y1) include acetyl, aryl, aralkyl, acyl, epoxysuccinyl and cholesteryl groups. Carboxy-derivative groups which can be present at the C-terminus of a peptide compound (i.e., can be Y2) include alcohol, aldehyde, epoxysuccinate, acid halide, carbonyl, halomethane, and diazomethane groups.

As used herein, "detectable label" or "imaging agent" refers to materials, which when covalently attached to a compound, permit detection of the compound, including but not limited to, detection in vivo in a patient to whom an Eph receptor binding agent has been administered. Suitable detectable labels are well known in the art and include, by way of example, radioisotopes, fluorescent labels (for example, fluorescein), and the like. The particular detectable label employed is not critical and is selected relative to the amount of label to be employed as well as the toxicity of the label at the amount of label employed. Selection of the label relative to such factors is well within the skill of the art.

Covalent attachment of the detectable label to the peptide or peptidomimetic is accomplished by conventional methods well known in the art. For example, when the $^{125}I$ radioisotope is employed as the detectable label, covalent attachment of $^{125}I$ to the peptide or the peptidomimetic can be achieved by incorporating the amino acid tyrosine into the peptide or peptidomimetic and then iodinating the peptide (see, for example, Weaner, et al. 1994 *Synthesis and Applications of Isotopically Labelled Compounds*, pp. 137-140). If tyrosine is not present in the peptide or peptidomimetic, incorporation of tyrosine to the N or C terminus of the peptide or peptidomimetic can be achieved by well known chemistry. Likewise, $^{32}P$ can be incorporated onto the peptide or peptidomimetic as a phosphate moiety through, for example, a hydroxyl group on the peptide or peptidomimetic using conventional chemistry.

By "selectively" is meant having a binding affinity for one or a few Eph receptor family members that is substantially greater than said binding affinity for the other known Eph receptor family members. As used in connection with selective binding affinity, "substantially greater" means at least a two-fold, at least a three-fold, at least a four-fold, at least a five-fold, at least a six-fold, at least a seven-fold, at least a eight-fold, at least a nine-fold, at least a ten-fold, at least a fifteen-fold, at least a twenty-fold, at least a thirty-fold, at least a forty-fold, at least a fifty-fold or at least a hundred-fold increase in the amount of ligand bound to a receptor.

As used herein, "Eph receptor binding agent" or "Eph receptor binding ligand" is a compound that binds to an Eph receptor. The compound may comprise any molecule that is capable of binding one or more Eph receptors. In some cases, the molecule that is capable of binding one or more Eph receptors is a peptide or a peptidomimetic. Such peptides or peptidomimetics can have a length of less than 10, less than 11, less than 12, less than 13, less than 14, less than 15, less than 20, less than 25, less than 30, less than 35, less than 40, less than 45, less than 50, less than 75, less than 100, less than 200, less than 300, less than 400 or less than 500 residues. The terms "Eph receptor binding agent" and "Eph receptor binding ligand" may be used interchangeably.

As used herein, "ephrin-B" includes any of the ephrins that are members of the ephrin-B ligand subclass As used herein the term "therapeutic agent" means an anticancer agent, neuroprotective agent, or other agent capable of having a desired therapeutic effect for a specific disease indication.

Anticancer agents described herein can be cytotoxic agents or cancer chemotherapeutic agents. As non limiting examples, cytotoxic agents that target a DNA associated process encompass cyclophosphamide, melphalan, mitomycin C, bizelesin, cisplatin, doxorubicin, etoposide, mitoxantrone, SN 38, Et 743, actinomycin D, bleomycin and TLK286. Cancer chemotherapeutic agents can be, without limitation, a taxane such as docetaxel; an anthracyclin such as doxorubicin; an alkylating agent; a vinca alkaloid; an anti metabolite; a platinum agent such as cisplatin or carboplatin; a steroid such as methotrexate; an antibiotic such as adriamycin; a isofamide; or a selective estrogen receptor modulator; an antibody such as trastuzumab.

Taxanes are chemotherapeutic agents useful in the combination treatment of the invention. Useful taxanes include, without limitation, docetaxel (Taxotere; Aventis Pharmaceuticals, Inc.; Parsippany, N.J.) and paclitaxel (Taxol; Bristol Myers Squibb; Princeton, N.J.). See, for example, Chan et al. 1999 *J Clin Oncol* 17:2341 2354, and Paridaens et al. 2000 *J Clin Oncol* 18:724.

Another cancer chemotherapeutic agent useful in the combination treatment of the invention is an anthracyclin such as doxorubicin, idarubicin or daunorubicin. Doxorubicin is a commonly used cancer chemotherapeutic agent and can be useful, for example, for treating breast cancer (Stewart and Ratain, In: "Cancer: Principles and Practice of Oncology" 5th ed., chap. 19, eds. DeVita, Jr. et al.; J. P. Lippincott 1997; Harris et al., In: "Cancer: Principles and practice of oncology," supra, 1997). In addition, doxorubicin has anti angiogenic activity (Folkman, 1997 *Nature Biotechnology* 15:510; Steiner, In: "Angiogenesis: Key principles Science, technology and medicine," pp. 449 454, eds. Steiner et al. Birkhauser Verlag, 1992), which can contribute to its effectiveness in treating cancer.

Alkylating agents such as melphalan or chlorambucil are cancer chemotherapeutic agents useful in the combination treatment of the invention. Similarly, a vinca alkaloid such as vindesine, vinblastine or vinorelbine; or an antimetabolite such as 5 fluorouracil, 5 fluorouridine or a derivative thereof are cancer chemotherapeutic agents useful in the combination treatment of the invention.

Platinum agents are chemotherapeutic agents useful in the combination treatment of the invention. Such a platinum agent can be, for example, cisplatin or carboplatin as described, for example, in Crown, 2001 *Seminars in Oncol* 28:28-37. Other cancer chemotherapeutic agents useful in the combination treatment of the invention include, without limitation, methotrexate, mitomycin C, adriamycin, ifosfamide and ansamycins.

Cancer chemotherapeutic agents used for treatment of breast cancer and other hormonally dependent cancers also can be used as an agent that antagonizes the effect of estrogen, such as a selective estrogen receptor modulator or an anti estrogen. The selective estrogen receptor modulator, tamoxifen, is a cancer chemotherapeutic agent that can be used in the combination treatment of the invention for treatment of breast cancer (Fisher et al. 1998 *J Natl Cancer Instit* 90:1371 1388).

A therapeutic agent useful in the combination treatment of the invention can be an antibody such as a humanized monoclonal antibody. As an example, the anti epidermal growth factor receptor 2 (HER2) antibody, trastuzumab (Herceptin; Genentech, South San Francisco, Calif.) is a therapeutic agent useful in a conjugate of the invention for treating HER2/neu overexpressing breast cancers (White et al. 2001 *Ann Rev Med* 52:125-141).

Another therapeutic agent useful in the invention also can be a cytotoxic agent, which, as used herein, is any molecule that directly or indirectly promotes cell death. Cytotoxic agents useful in the invention include, without limitation, small molecules, polypeptides, peptides, peptidomimetics, nucleic acid molecules, cells and viruses. As non limiting examples, cytotoxic agents useful in the invention include cytotoxic small molecules such as doxorubicin, docetaxel or trastuzumab; antimicrobial peptides such as those described further below; pro-apoptotic polypeptides such as caspases and toxins, for example, caspase 8; diphtheria toxin A chain, *Pseudomonas* exotoxin A, cholera toxin, ligand fusion toxins such as DAB389EGF, *ricinus communis* toxin (ricin); and cytotoxic cells such as cytotoxic T cells. See, for example, Martin et al. 2000 *Cancer Res* 60:3218-3224; Kreitman and Pastan 1997 *Blood* 90:252-259; Allam et al. 1997 *Cancer Res* 57:2615-2618; Osborne and Coronado Heinsohn 1996 *Cancer J Sci Am* 2:175. One skilled in the art understands that these and additional cytotoxic agents described herein or known in the art can be useful as therapeutic agents of the invention.

Neuroprotective agents are well known in the art and can be compounds which prevent or delay the death of neuronal cells. As nonlimiting examples, neuroprotective agents can be anti-apoptotic compounds such as small molecule drugs, peptides, proteins, antibodies or a combination thereof. Neuroprotective agents may act through interference with one or more apoptotic or necrotic pathways, activation of neural growth hormone receptors or modulation of ion channels. One skilled in the art understands that these and additional neuroprotective agents described herein or known in the art can be useful as therapeutic agents of the invention.

Eph Receptor Binding Agents

Embodiments of the invention provide agents that bind to the Eph receptors. Many of the compounds described herein selectively bind to only one or a limited number of the sixteen known receptors of the Eph receptor family. The Eph receptor binding agents can be small molecule drugs, peptides, or peptidomimetics. The Eph receptor binding agents may be natural compounds or synthetic compounds. Many of the compounds described herein also bind Eph receptors with high affinity and can act as either an Eph receptor agonist or antagonist. The compounds described herein include "lead" compounds and "derivative" compounds constructed so as to have the same or similar molecular structure or shape as the lead compounds but that differ from the lead compounds either with respect to susceptibility to hydrolysis or proteolysis and/or with respect to other biological properties, such as increased affinity for the receptor, or having additional biological properties unrelated to the target Eph receptor.

Preparation of Peptides and Peptidomimetics

1. Solid Phase Synthesis

The peptides described herein can be prepared by classical methods known in the art, for example, by using standard solid phase techniques. The standard methods include exclusive solid phase synthesis, partial solid phase synthesis methods, fragment condensation, classical solution synthesis, and even by recombinant DNA technology. See, for example, Merrifield, 1963 *J Am Chem Soc* 85:2149, incorporated herein by reference. On solid phase, the synthesis is typically commenced from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the trade name BIO-BEADS SX-1 by BioRad Laboratories, Richmond, Calif., and the preparation of the hydroxymethyl resin is described by Bodonszky, et al. 1966 *Chem Ind (London)* 38:1597. The benzhydrylamine (BHA) resin has been described by Pietta and Marshall, 1970 *Chem Commn* 650, and is commercially available from Beckman Instruments, Inc., Palo Alto, Calif., in the hydrochloride form.

Thus, compounds can be prepared by coupling an alpha-amino protected amino acid to the chloromethylated resin with the aid of, for example, cesium bicarbonate catalyst, according to the method described by Gisin, 1973 *Helv Chim Acta* 56:1467. After the initial coupling, the alpha-amino protecting group is removed by a choice of reagents including trifluoroacetic acid (TFA) or hydrochloric acid (HCl) solutions in organic solvents at room temperature.

The alpha-amino protecting groups are those known to be useful in the art of stepwise synthesis of peptides. Included are acyl type protecting groups (for example, formyl, trifluoroacetyl, acetyl), aromatic urethane type protecting groups (for example benzyloxycarbonyl (Cbz) and substituted Cbz), aliphatic urethane protecting groups (for example, t-butyloxycarbonyl (Boc), isopropyloxycarbonyl, cyclohexyloxycarbonyl) and alkyl type protecting groups (for example, benzyl, triphenylmethyl). Boc and Fmoc are preferred protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

The side chain protecting groups for Tyr include tetrahydropyranyl, tert-butyl, trityl, benzyl, Cbz, Z—Br-Cbz, and 2,5-dichlorobenzyl. The side chain protecting groups for Asp include benzyl, 2,6-dichlorobenzyl, methyl, ethyl, and cyclohexyl. The side chain protecting groups for Thr and Ser include acetyl, benzoyl, trityl, tetrahydropyranyl, benzyl, 2,6-dichlorobenzyl, and Cbz. The side chain protecting group for Thr and Ser is benzyl. The side chain protecting groups for Arg include nitro, Tosyl (Tos), Cbz, adamantyloxycarbonyl mesitoylsulfonyl (Mts), or Boc. The side chain protecting groups for Lys include Cbz, 2-chlorobenzyloxycarbonyl (2Cl-Cbz), 2-bromobenzyloxycarbonyl (2-BrCbz), Tos, or Boc.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride ($CH_2Cl_2$), dimethyl formamide (DMF) mixtures.

After the desired amino acid sequence has been completed, the desired peptide is decoupled from the resin support by treatment with a reagent such as trifluoroacetic acid or hydrogen fluoride (HF), which not only cleaves the peptide from the resin, but also cleaves all remaining side chain protecting groups. When the chloromethylated resin is used, hydrogen fluoride treatment results in the formation of the free peptide acids. When the benzhydrylamine resin is used, hydrogen fluoride treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

These solid phase peptide synthesis procedures are well known in the art and further described by J. M. Stewart and J. D. Young, 1984 *Solid Phase Peptide Syntheses* 2nd Ed., Pierce Chemical Company.

Using the "encoded synthetic library" or "very large scale immobilized polymer synthesis" system described in U.S. patent application Ser. No. 07/492,462, filed Mar. 7, 1990; Ser. No. 07/624,120, filed Dec. 6, 1990; and Ser. No. 07/805,727, filed Dec. 6, 1991; one can not only determine the minimum size of a peptide with such activity, one can also make all of the peptides that form the group of peptides that differ from the preferred motif (or the minimum size of that motif) in one, two, or more residues. This collection of peptides can then be screened for ability to bind to members of the Eph receptor family including, but not limited to, EphB1, EphB2 and EphB4. It will be appreciated that this immobilized polymer synthesis system or other peptide synthesis methods can also be used to synthesize truncation analogs and deletion analogs and combinations of truncation and deletion analogs of all of the peptide compounds of the invention.

2. Synthetic Amino Acids

These procedures can also be used to synthesize peptides in which amino acids other than the 20 naturally occurring, genetically encoded amino acids are substituted at one, two, or more positions of any of the compounds of the invention. For instance, naphthylalanine can be substituted for tryptophan, facilitating synthesis. Other synthetic amino acids that can be substituted into the peptides of the present invention include L-hydroxypropyl, L-3,4-dihydroxy-phenylalanyl, d amino acids such as L-d-hydroxylysyl and D-d-methylalanyl, L-a-methylalanyl, β amino acids, and isoquinolyl. D amino acids and non-naturally occurring synthetic amino acids can also be incorporated into the peptides of the present invention (see, for example, Roberts, et al. 1983 *Unusual Amino/Acids in Peptide Synthesis* 5:341-449).

One can replace the naturally occurring side chains of the 20 genetically encoded amino acids (or D amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic. In particular, proline analogs in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (for example, morpholino), oxazolyl, piperazinyl (for example, 1-piperazinyl), piperidyl (for example, 1-piperidyl, piperidino), pyranyl, pyrazinyl, pyrazolidinyl, pyrazolinyl, pyrazolyl, pyridazinyl, pyridyl, pyrimidinyl, pyrrolidinyl (for example, 1-pyrrolidinyl), pyrrolinyl, pyrrolyl, thiadiazolyl, thiazolyl, thienyl, thiomorpholinyl (for example, thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify the peptides of the instant invention by phosphorylation (see, for example, W. Bannwarth, et al. 1996 *Biorganic and Medicinal Chemistry Let-* ters 6:2141-2146), and other methods for making peptide derivatives of the compounds of the present invention are described in Hruby, et al. 1990 *Biochem J* 268:249-262. Thus, the peptide compounds of the invention also serve as a basis to prepare peptidomimetics with similar biological activity.

3. Terminal Modifications

Those of skill in the art recognize that a variety of techniques are available for constructing peptidomimetics with the same or similar desired biological activity as the corresponding peptide compound but with more favorable activity than the peptide with respect to solubility, stability, and susceptibility to hydrolysis and proteolysis. See, for example, Morgan, et al. 1989 *Ann Rep Med Chem* 24:243-252. The following describes methods for preparing peptidomimetics modified at the N-terminal amino group, the C-terminal carboxyl group, and/or changing one or more of the amido linkages in the peptide to a non-amido linkage. It being understood that two or more such modifications can be coupled in one peptidomimetic structure (for example, modification at the C-terminal carboxyl group and inclusion of a —CH2-carbamate linkage between two amino acids in the peptide).

1). N-Terminal Modifications

The peptides typically are synthesized as the free acid but, as noted above, could be readily prepared as the amide or ester. One can also modify the amino and/or carboxy terminus of the peptide compounds to produce other useful compounds. Amino terminus modifications include methylation (i.e., —NHCH$_3$ or —NH(CH$_3$)$_2$), acetylation, adding a benzyloxycarbonyl group, or blocking the amino terminus with any blocking group containing a carboxylate functionality defined by RCOO—, where R is selected from the group consisting of naphthyl, acridinyl, steroidyl, and similar groups. Carboxy terminus modifications include replacing the free acid with a carboxamide group or forming a cyclic lactam at the carboxy terminus to introduce structural constraints.

Amino terminus modifications are as recited above and include alkylating, acetylating, adding a carbobenzoyl group, forming a succinimide group, etc. (See, for example, Murray, et al. 1995 *Burger's Medicinal Chemistry and Drug Discovery* 5th ed., Vol. 1, Manfred E. Wolf, ed., John Wiley and Sons, Inc.) Specifically, the N-terminal amino group can then be reacted as follows:

(a) to form an amide group of the formula RC(O)NH— where R is as defined above by reaction with an acid halide [for example, RC(O)Cl or symmetric anhydride. Typically, the reaction can be conducted by contacting about equimolar or excess amounts (for example, about 5 equivalents) of an acid halide to the peptide in an inert diluent (for example, dichloromethane) preferably containing an excess (for example, about 10 equivalents) of a tertiary amine, such as diisopropylethylamine, to scavenge the acid generated during reaction. Reaction conditions are otherwise conventional (for example, room temperature for 30 minutes). Alkylation of the terminal amino to provide for a lower alkyl N-substitution followed by reaction with an acid halide as described above will provide for N-alkyl amide group of the formula RC(O)NR—;

(b) to form a succinimide group by reaction with succinic anhydride. As before, an approximately equimolar amount or an excess of succinic anhydride (for example, about 5 equivalents) can be employed and the amino group is converted to the succinimide by methods well known in the art including the use of an excess (for example, ten equivalents) of a tertiary amine such as diisopropylethylamine in a suitable inert solvent (for example, dichloromethane). See, for example, Wollenberg, et al., U.S. Pat. No. 4,612,132 which is incorporated herein by reference in its entirety. It is understood that the succinic group can be substituted with, for example, C$_2$-C$_6$ alkyl or —SR substituents which are prepared in a conventional manner to provide for substituted succinimide at the N-terminus of the peptide. Such alkyl substituents are prepared by reaction of a lower olefin (C$_2$-C$_6$) with maleic anhydride in the manner described by Wollenberg, et al., supra and —SR substituents are prepared by reaction of RSH with maleic anhydride where R is as defined above;

(c) to form a benzyloxycarbonyl-NH— or a substituted benzyloxycarbonyl-NH— group by reaction with approximately an equivalent amount or an excess of CBZ—Cl (i.e., benzyloxycarbonyl chloride) or a substituted CBZ—Cl in a suitable inert diluent (for example, dichloromethane) preferably containing a tertiary amine to scavenge the acid generated during the reaction;

(d) to form a sulfonamide group by reaction with an equivalent amount or an excess (for example, 5 equivalents) of R—S(O)$_2$Cl in a suitable inert diluent (dichloromethane) to convert the terminal amine into a sulfonamide where R is as defined above. Preferably, the inert diluent contains excess tertiary amine (for example, ten equivalents) such as diisopropylethylamine, to scavenge the acid generated during reaction. Reaction conditions are otherwise conventional (for example, room temperature for 30 minutes);

(e) to form a carbamate group by reaction with an equivalent amount or an excess (for example, 5 equivalents) of R—OC(O)Cl or R—OC(O)OC$_6$H$_4$-p-NO$_2$ in a suitable inert diluent (for example, dichloromethane) to convert the terminal amine into a carbamate where R is as defined above. Preferably, the inert diluent contains an excess (for example, about 10 equivalents) of a tertiary amine, such as diisopropylethylamine, to scavenge any acid generated during reaction. Reaction conditions are otherwise conventional (for example, room temperature for 30 minutes); and (f) to form a urea group by reaction with an equivalent amount or an excess (for example, 5 equivalents) of R—N═C═O in a suitable inert diluent (for example, dichloromethane) to convert the terminal amine into a urea (i.e., RNHC(O)NH—) group where R is as defined above. Preferably, the inert diluent contains an excess (for example, about 10 equivalents) of a tertiary amine, such as diisopropylethylamine. Reaction conditions are otherwise conventional (for example, room temperature for about 30 minutes).

2). C-Terminal Modifications

In preparing peptidomimetics wherein the C-terminal carboxyl group is replaced by an ester (i.e., —C(O)OR where R is as defined above), the resins used to prepare the peptide acids are employed, and the side chain protected peptide is cleaved with base and the appropriate alcohol, for example, methanol. Side chain protecting groups are then removed in the usual fashion by treatment with hydrogen fluoride to obtain the desired ester.

In preparing peptidomimetics wherein the C-terminal carboxyl group is replaced by the amide —C(O)NR$^3$R$^4$, a benzhydrylamine resin is used as the solid support for peptide synthesis. Upon completion of the synthesis, hydrogen fluoride treatment to release the peptide from the support results directly in the free peptide amide (i.e., the C-terminus is —C(O)NH$_2$). Alternatively, use of the chloromethylated resin during peptide synthesis coupled with reaction with ammonia to cleave the side chain protected peptide from the support yields the free peptide amide and reaction with an alkylamine or a dialkylamine yields a side chain protected alkylamide or dialkylamide (i.e., the C-terminus is —C(O)NRR$^1$ where R and R$^1$ are as defined above). Side chain protection is then removed in the usual fashion by treatment with hydrogen fluoride to give the free amides, alkylamides, or dialkylamides.

In another alternative embodiment, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride ($CH_2Cl_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Such methods are well known in the art.

One can also cyclize the peptides of the invention, or incorporate a desamino or descarboxy residue at the termini of the peptide, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof.

In addition to the foregoing N-terminal and C-terminal modifications, the peptide compounds described herein, including peptidomimetics, can advantageously be modified with or covalently coupled to one or more of a variety of hydrophilic polymers. It has been found that when the peptide compounds are derivatized with a hydrophilic polymer, their solubility and circulation half-lives are increased and their immunogenicity is masked. Quite surprisingly, the foregoing can be accomplished with little, if any, diminishment in their binding activity. Nonproteinaceous polymers suitable for use include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, more preferably from about 2,000 to about 40,000 daltons and, even more preferably, from about 5,000 to about 20,000 daltons. In preferred embodiments, such hydrophilic polymers have average molecular weights of about 5,000 daltons, 10,000 daltons and 20,000 daltons.

The peptide compounds can be derivatized with or coupled to such polymers using any of the methods set forth in Zalipsky, S. 1995 *Bioconjugate Chem* 6:150-165; Monfardini, C, et al. 1995 *Bioconjugate Chem* 6:62-69; U.S. Pat. Nos. 4,640,835; 4,496,689; 4,301,144; 4,670,417; 4,791,192; 4,179,337 or WO 95/34326, all of which are incorporated by reference in their entirety herein.

In one embodiment, the peptide compounds are derivatized with polyethylene glycol (PEG). PEG is a linear, water-soluble polymer of ethylene oxide repeating units with two terminal hydroxyl groups. PEGs are classified by their molecular weights which typically range from about 500 daltons to about 40,000 daltons. In a presently preferred embodiment, the PEGs employed have molecular weights ranging from 5,000 daltons to about 20,000 daltons. PEGs coupled to the peptide compounds of the present invention can be either branched or unbranched. (See, for example, Monfardini, C. et al. 1995 *Bioconjugate Chem* 6:62-69). PEGs are commercially available from Shearwater Polymers, Inc. (Huntsville, Ala.), Sigma Chemical Co. and other companies. Such PEGs include, but are not limited to, monomethoxypolyethylene glycol (MePEG-OH), monomethoxypolyethylene glycol-succinate (MePEG-S), monomethoxypolyethylene glycol-succinimidyl succinate (MePEG-S—NHS), monomethoxypolyethylene glycol-amine (MePEG-NH2), monomethoxypolyethylene glycol-tresylate (MePEG-TRES), and monomethoxypolyethylene glycol-imidazolyl-carbonyl (MePEG-IM).

Briefly, in one exemplar embodiment, the hydrophilic polymer which is employed, for example, PEG, is preferably capped at one end by an unreactive group such as a methoxy or ethoxy group. Thereafter, the polymer is activated at the other end by reaction with a suitable activating agent, such as cyanuric halides (for example, cyanuric chloride, bromide or fluoride), diimadozle, an anhydride reagent (for example, a dihalosuccinic anhydride, such as dibromosuccinic anhydride), acyl azide, p-diazoiumbenzyl ether, 3-(p-diazoniumphenoxy)-2-hydroxypropylether) and the like. The activated polymer is then reacted with a peptide compound as described herein to produce a peptide compound derivatized with a polymer. Alternatively, a functional group in the peptide compounds of the invention can be activated for reaction with the polymer, or the two groups can be joined in a concerted coupling reaction using known coupling methods. It will be readily appreciated that the peptide compounds of the invention can be derivatized with PEG using a myriad of other reaction schemes known to and used by those of skill in the art.

In some embodiments, the derivatized peptides have an activity that is about 0.1 to about 0.01-fold that of the unmodified peptides. In more other embodiments, the derivatized peptides have an activity that is about 0.1 to about 1-fold that of the unmodified peptides. In still other embodiments, the derivatized peptides have an activity that is greater than the unmodified peptides.

Peptides suitable for use in this embodiment generally include the peptides, i.e., ligands, that bind to members of the Eph receptor family including, but not limited to, EphB1, EphB2, EphB3 or EphB4. Such peptides typically comprise about 50 amino acid residues or less and, more preferably, about 20 amino acid residues or less. Hydrophilic polymers suitable for use in the present invention include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, more preferably from about 2,000 to about 40,000 daltons and, even more preferably, from about 5,000 to about 20,000 daltons. In some embodiments, such hydrophilic polymers have average molecular weights of about 5,000 daltons, 10,000 daltons and 20,000 daltons. The peptide compounds can be derivatized with using the methods described above and in the cited references.

4. Backbone Modifications

Other methods for making peptide derivatives of the compounds are described in Hruby, et al. 1990 *Biochem J* 268(2): 249-262, incorporated herein by reference. Thus, the peptide compounds also serve as structural models for non-peptidic compounds with similar biological activity. Those of skill in the art recognize that a variety of techniques are available for constructing compounds with the same or similar desired biological activity as the lead peptide compound but with more favorable activity than the lead with respect to solubility, stability, and susceptibility to hydrolysis and proteolysis.

See Morgan, et al. 1989 *Ann Rep Med Chem* 24:243-252, incorporated herein by reference. These techniques include replacing the peptide backbone with a backbone composed of phosphonates, amidates, carbamates, sulfonamides, secondary amines, and N-methylamino acids.

Peptidomimetics wherein one or more of the peptidyl linkages [—C(O)NH—] have been replaced by such linkages as a —$CH_2$-carbamate linkage, a phosphonate linkage, a —$CH_2$-sulfonamide linkage, a urea linkage, a secondary amine (—$CH_2$NH—) linkage, and an alkylated peptidyl linkage [—C(O)$NR^6$— where $R^6$ is lower alkyl] are prepared during conventional peptide synthesis by merely substituting a suitably protected amino acid analogue for the amino acid reagent at the appropriate point during synthesis.

Suitable reagents include, for example, amino acid analogues wherein the carboxyl group of the amino acid has been replaced with a moiety suitable for forming one of the above linkages. For example, if one desires to replace a —C(O)NR— linkage in the peptide with a —$CH_2$-carbamate linkage (—$CH_2$OC(O)NR—), then the carboxyl (—COOH) group of a suitably protected amino acid is first reduced to the —$CH_2$OH group which is then converted by conventional methods to a —OC(O)Cl functionality or a para-nitrocarbonate —OC(O)O—$C_6H_4$-p-$NO_2$ functionality. Reaction of either of such functional groups with the free amine or an alkylated amine on the N-terminus of the partially fabricated peptide found on the solid support leads to the formation of a —$CH_2$OC(O)NR— linkage. For a more detailed description of the formation of such —$CH_2$-carbamate linkages, see —Cho, et al. 1993 *Science* 261:1303-1305.

Similarly, replacement of an amido linkage in the peptide with a phosphonate linkage can be achieved in the manner set forth in U.S. patent application Ser. Nos. 07/943,805, 08/081,577, and 08/119,700, the disclosures of which are incorporated herein by reference in their entirety.

Replacement of an amido linkage in the peptide with a —$CH_2$-sulfonamide linkage can be achieved by reducing the carboxyl (—COON) group of a suitably protected amino acid to the —$CH_2$OH group and the hydroxyl group is then converted to a suitable leaving group such as a tosyl group by conventional methods. Reaction of the tosylated derivative with, for example, thioacetic acid followed by hydrolysis and oxidative chlorination will provide for the —$CH_2S(O)_2$Cl functional group which replaces the carboxyl group of the otherwise suitably protected amino acid. Use of this suitably protected amino acid analogue in peptide synthesis provides for inclusion of a —$CH_2S(O)_2$NR— linkage, which replaces the amido linkage in the peptide thereby providing a peptidomimetic. For a more complete description on the conversion of the carboxyl group of the amino acid to a —$CH_2S(O)_2$Cl group, see, for example, Weinstein, B., 1983 *Chemistry & Biochemistry of Amino Acids, Peptides and Proteins* Vol. 7, pp. 267-357, Marcel Dekker, Inc., New York, which is incorporated herein by reference.

Replacement of an amido linkage in the peptide with a urea linkage can be achieved in the manner set forth in U.S. patent application Ser. No. 08/147,805 which application is incorporated herein by reference in its entirety.

Secondary amine linkages wherein a —$CH_2$NH— linkage replaces the amido linkage in the peptide can be prepared by employing, for example, a suitably protected dipeptide analogue wherein the carbonyl bond of the amido linkage has been reduced to a $CH_2$ group by conventional methods. For example, in the case of diglycine, reduction of the amide to the amine will yield after deprotection $H_2NCH_2CH_2NHCH_2COOH$ which is then used in N-protected form in the next coupling reaction. The preparation of such analogues by reduction of the carbonyl group of the amido linkage in the dipeptide is well known in the art (see, for example, M. W. Remington 1994 *Meth Mol Bio* 35:241-247).

The suitably protected amino acid analogue is employed in the conventional peptide synthesis in the same manner as would the corresponding amino acid. For example, typically about 3 equivalents of the protected amino acid analogue are employed in this reaction. An inert organic diluent such as methylene chloride or DMF is employed and, when an acid is generated as a reaction by-product, the reaction solvent will typically contain an excess amount of a tertiary amine to scavenge the acid generated during the reaction. One particularly preferred tertiary amine is diisopropylethylamine which is typically employed in about 10-fold excess. The reaction results in incorporation into the peptidomimetic of an amino acid analogue having a non-peptidyl linkage. Such substitution can be repeated as desired such that from zero to all of the amido bonds in the peptide have been replaced by non-amido bonds.

One can also cyclize the peptides, or incorporate a desamino or descarboxy residue at the termini of the peptide, so that there is no terminal amino or carboxyl group, to decrease susceptibility to proteases or to restrict the conformation of the peptide. C-terminal functional groups of the compounds include amide, amide lower alkyl, amide di(lower alkyl), lower alkoxy, hydroxy, and carboxy, and the lower ester derivatives thereof, and the pharmaceutically acceptable salts thereof.

5. Disulfide Bond Formation

The compounds may exist in a cyclized form with an intramolecular disulfide bond between the thiol groups of the cysteines. Alternatively, an intermolecular disulfide bond between the thiol groups of the cysteines can be produced to yield a dimeric (or higher oligomeric) compound. One or more of the cysteine residues may also be substituted with a homocysteine.

Other embodiments of this invention include analogs of these disulfide derivatives in which one of the sulfurs has been replaced by a $CH_2$ group or other isostere for sulfur. These analogs can be made via an intramolecular or intermolecular displacement, using methods known in the art.

Alternatively, the amino-terminus of the peptide can be capped with an alpha-substituted acetic acid, wherein the alpha substituent is a leaving group, such as an α-haloacetic acid, for example, α-chloroacetic acid, α-bromoacetic acid, or α-iodoacetic acid. The compounds of the present invention can be cyclized or dimerized via displacement of the leaving group by the sulfur of the cysteine or homocysteine residue. See, for example, Andreu, et al. 1994 *Meth Mol Bio* 35(7): 91-169; Barker, et al. 1992 *J Med Chem* 35:2040-2048; and Or, et al. 1991 *J Org Chem* 56:3146-3149, each of which is incorporated herein by reference.

The peptides may also be prepared by recombinant DNA techniques well known in the art.

Modulation of Eph Receptors with Eph Receptor Binding Compounds

The Eph receptor binding compounds described herein are capable of modulating Eph activity in a cell. The Eph receptor binding compounds that modulate Eph activity comprise a peptide or peptidomimetic described herein which binds to one or more members of the Eph receptor family. In some embodiments of the present invention the Eph receptor binding compounds include only a single peptide or peptidomimetic described herein. In some embodiments of the present invention, cells are contacted with an amount of Eph receptor binding compound in an amount that is effective to cause the phosphorylation of the receptor thereby activating downstream signaling events. In some embodiments, cells are contacted with an amount of Eph receptor binding compound in an amount that is effective to prevent phosphorylation of the receptor by ephrin ligands, thereby inhibiting receptor activity. In other embodiments, the cells can be contacted with an Eph receptor binding compound in an amount that is effective to cause activation or inactivation of downstream signaling events. The amount of Eph receptor binding compound that is effective to activate or inactivate downstream signaling events includes concentrations of at least 0.05 µM, at least 0.1 µM, at least 0.2 µM, at least 0.3 µM, at least 0.4 µM, at least 0.5 µM, at least 0.6 µM, at least 0.7 µM, at least 0.8 µM, at least 0.9 µM, at least 1 WA, at least 5 µM, at least 10 µM, at least 20 at least 30 µM, at least 40 µM, at least 50 µM, at least 60 µM, at least 70 µM, at least 80 µM, at least 90 µM, at least 100 µM or at least 200 Determination of other effective concentrations not described herein can be readily determined by one of ordinary skill in the art.

In some embodiments of the present invention, the Eph receptor of interest is modulated in cells both in vitro and in vivo. With respect to either application, the cells can be any cells that express at least one member of the Eph family of receptors including but not limited to human cells.

In other embodiments, receptors of the EphB sub-family are modulated. Such receptors include EphB3, EphB2, EphB3, EphB4, EphB5 and EphB6. In certain embodiments, cells expressing the EphB1 receptor are contacted with effective amounts of peptides, peptidomimetics or small molecules described herein so as to modulate the activity of this receptor and subsequent downstream signaling events. In other embodiments, cells expressing the EphB2 receptor are contacted with effective amounts of peptides, peptidomimetics or small molecules described herein so as to modulate the activity of this receptor and subsequent downstream signaling events. In other embodiments, cells expressing the EphB4 receptor are contacted with effective amounts of peptides, peptidomimetics or small molecules described herein so as to modulate the activity of this receptor and subsequent downstream signaling events.

Stimulation of certain members of Eph family receptors have been implicated in the activation of apoptosis (programmed cell death). Accordingly, activation of programmed cell death in certain cells overexpressing an Eph receptor, such as certain types of neoplastic cells, would be advantageous for the selective killing of undesirable cell populations. Furthermore, an Eph receptor binding compound that acts as a selective agonist of a specific overexpressed Eph receptor in a cell type targeted for programmed cell death would provide a method to eliminate target cells without killing nontarget cells.

In some embodiments of the present invention, methods of administering an Eph receptor binding compound that acts as a selective agonist or antagonist of a specific member of the Eph receptor family are contemplated. In some embodiments, selective agonists, such as a peptide, peptidomimetics or small molecules described herein, can be used to activate programmed cell death by administering an effective amount of such peptide, peptidomimetic or small molecule to mammals, including humans. In certain embodiments, the agonist binds to an EphB1, EphB2 or EphB4 receptors thereby competitively inhibiting ephrin-B1 or ephrin-B2 binding to the receptor. In other embodiments, binding of the agonist stimulates the phosphorylation of the receptor.

The effective amount of agonist that is administered to the mammal can range from about 0.001 mg to about 50 mg/kg of body weight per day. The effective amount will depend on factors including, but not limited to, the route by which the agonist is administered, binding affinity of the agonist, Eph receptor expression level in target cells, and Eph receptor expression level in non-target cells. It will be appreciated, however, that determination of an effective amount of agonist can be readily determined by one of ordinary skill in the art.

Eph Receptor Binding Compounds as Therapeutics and Therapeutic Delivery Agents

The Eph receptor binding compounds described herein can also be administered to warm blooded animals, including humans, to modulate Eph receptors in vivo. For example, certain peptides disclosed herein can be used to selectively activate or inhibit EphB1, EphB2, EphB3 or EphB4. Thus, the present invention encompasses methods for therapeutic treatment of Eph related disorders that comprise administering such a compound in amounts sufficient to activate or inhibit an Eph receptor in vivo.

Targeting Eph receptors also allows therapeutic intervention in cancer and other diseases. The Eph receptor binding compounds described herein can be used to deliver cytotoxic agents to blood vessels of diseased tissues. Indeed, vascular-targeted peptides coupled to chemotherapeutic drugs, toxins, or pro-apoptotic peptides can decrease tumor growth, suppress clinical arthritis, or destroy prostate tissue (Arap, W. et al. 1998 Science 279:377-380; Olson, T. A. et al. 1997 Int J Cancer 73:865-870; Ellerby, H. M. et al. 1999 Nat Med 5:1032-1038; Arap, W. et al. 2002 PNAS USA 99:1527-1531; Gerlag, D. M. et al. 2001 Arthritis Research 3:357-361). For example, tyrosine phosphorylation of EphA2 caused by agonists mediates internalization of the receptor and the agonist (Zantek, N. D. et al. 1999 Cell Growth Differ 10:629-638; Carles-Kinch, K. et al. 2002 Cancer Res 62:2840-2847; Van der Geer, P. et al. 1994 Annu Rev Cell Biol 10:251-337), therefore, toxic or pro-apoptotic substances can be delivered intracellularly to selectively kill cells (Ellerby, H. M. et al. 1999 Nat Med 5:1032-1038). Furthermore, activation of EphA2 induced by the Eph receptor binding compounds described herein can reduce proliferation, invasiveness, and metastatic behavior of EphA2-expressing cancer cells (Zantek, N. D. et al. 1999 Cell Growth Differ 10:629-638; Carles-Kinch, K. et al. 2002 Cancer Res 62:2840-2847; Miao, H. et al. Nature 2000 Cell Biol 2:62-69). It is known in the art that EphA2 activation correlates with decreased malignancy of breast and prostate cancer cells and reverses the transforming effects of EphA2 overexpression (Zelinski, D. P. et al. 2002 J Cell Biochem 85:714-720; Zantek, N. D. et al. 1999 Cell Growth Differ 10:629-638; Carles-Kinch, K. et al. 2002 Cancer Res 62:2840-2847). EphA2 activation by the compositions disclosed herein can sensitize cells to apoptotic stimuli when the Eph receptor binding compounds described herein are used to deliver cytotoxic agents (Dohn, M. et al. 2001 Oncogene 20:6503-6515).

The terms "tumor" and "neoplastic disease" as used herein; are understood to mean any abnormal or uncontrolled growth of cells which may result in the invasion of normal tissues. It is contemplated also that the term embraces abnormal or uncontrolled cell growths that have metastasized, i.e., abnormal cells that have spread from a primary location in the body (i.e., primary tumor) to a secondary location spatially removed from the primary tumor.

It is contemplated that the Eph receptor binding compounds described herein can be used in the treatment of a variety of tumors, for example, breast cancer, prostate cancer, kidney cancer, Karposi's sarcoma, colorectal cancer, cervical cancer, ovarian cancer, endometrial cancer, lung cancer, brain tumor, cutaneous T-cell lymphoma, cancer of the head and neck, cancers of the aerodigestive pathway, pancreatic cancer, melanoma, bladder cancer, sarcomas, leukoplakias, acute promyelocytic leukemia and the like, tumors that are mesenchymal in origin (sarcomas) i.e., fibrosarcomas; myxosarcomas; liposarcomas; chondrosarcomas; osteogenic sarcomas; angiosarcomas; endotheliosarcomas; lymphangiosarcomas; synoviosarcomas; mesotheliomas; mesotheliosarcomas; Ewing's tumors; myelogenous leukemias; monocytic leukemias; malignant lymphomas; lymphocytic leukemias; plasmacytomas; leiomyosarcomas and rhabdomyosarcoma.

In addition, it is contemplated that the Eph receptor binding compounds described herein can be used in the treatment of tumors that are epithelial in origin (carcinomas) i.e., squamous cell or epidermal carcinomas; basal cell carcinomas; sweat gland carcinomas; sebaceous gland carcinomas; adenocarcinomas; papillary carcinomas; papillary adenocarcinomas; cystadenocarcinomas; medullary carcinomas; undifferentiated carcinomas (simplex carcinomas); bronchogenic carcinomas; bronchial carcinomas; melanocarcinomas; renal cell carcinomas; hepatocellular carcinomas; bile duct carcinomas; papillary carcinomas; transitional cell carcinomas; squamous cell carcinomas; choriocarcinomas; seminomas; embryonal carcinomas malignant teratomas and teratocarcinomas.

Some embodiments of the present invention contemplate conjugates that comprise a therapeutic agent linked to an Eph receptor binding compound, such as the peptides, peptidomimetics and small molecules described herein. Such conjugates can be delivered to target cells that express an appropriate Eph receptor by administering an appropriate conjugate to an animal in need of treatment. In some embodiments, the therapeutic agent is responsible for the treatment. In other embodiments, both the therapeutic agent and the Eph receptor binding compound contribute to the treatment. In some embodiments the therapeutic agent is an imaging agent.

The Eph receptor binding compound which binds to the Eph receptor of interest is linked to a therapeutic agent with a linker. The linker can be any bond, small molecule, or other vehicle that allows the Eph receptor binding compound and the therapeutic agent to be targeted to the same area, tissue, or cell. Preferably, the linker is cleavable.

In one embodiment the linker is a chemical bond between one or more Eph receptor binding compounds and one or more therapeutic agents. Thus, the bond may be covalent or ionic. An example of a conjugate where the linker is a chemical bond would be a fusion protein. In one embodiment, the chemical bond is a pH sensitive bond. Alternatively, the bond may not be pH sensitive, but may be cleavable by a specific enzyme or chemical which is subsequently added or naturally found in the microenvironment of the targeted site Alternatively, the bond may be a bond that is cleaved under reducing conditions, for example a disulfide bond. Alternatively, the bond may not be cleavable.

Any kind of pH cleavable or pH sensitive linker may be used. Examples of acid cleavable bonds include, but are not limited to: a class of organic acids known as cis-polycarboxylic alkenes. This class of molecule contains at least three carboxylic acid groups (COOH) attached to a carbon chain that contains at least one double bond. These molecules as well as how they are made and used is disclosed in Shen, et al. U.S. Pat. No. 4,631,190 (herein incorporated by reference). Alternatively, molecules such as amino-sulfhydryl cross-linking reagents which are cleavable under mildly acidic conditions may be used. These molecules are disclosed in Blather et al. U.S. Pat. No. 4,569,789 (herein incorporated by reference).

Alternatively, the cleavable linker may be a time-release bond, such as a biodegradable, hydrolyzable bond. Typical biodegradable carrier bonds include esters, amides or urethane bonds, so that typical carriers are polyesters, polyamides, polyurethanes and other condensation polymers having a molecular weight between about 5,000 and 1,000,000. Examples of these carriers/bonds are shown in Peterson, et al. U.S. Pat. No. 4,356,166 (herein incorporated by reference). Other acid cleavable linkers may be found in U.S. Pat. Nos. 4,569,789 and 4,631,190 (herein incorporated by reference) or Blattler et al. 1985 *Biochemistry* 24:1517-1525. The linkers are cleaved by natural acidic conditions, or alternatively, acid conditions can be induced at a target site as explained in Abrams et al. U.S. Pat. No. 4,171,563 (herein incorporated by reference).

Examples of linking reagents which contain cleavable disulfide bonds (reducible bonds) include, but are not limited to "DPDPB", 1,4-di-[3'-(2'-pyridyldithio)propionamido]butane; "SADP", (N-succinimidyl (4-azidophenyl)1,3'-dithiopropionate); "Sulfo SADP" (Sulfosuccinimidyl (4-azidophenyldithio)propionate; "DSP" Dithio bis (succinimidylproprionate); "DTSSP"-3,3'-Dithio bis (sulfosuccinimidylpropionate); "DTBP"-dimethyl 3,3'-dithiobispropionimidate-2 HCl, all available from Pierce Chemicals (Rockford, Ill.).

Examples of linking reagents cleavable by oxidation are "DST"-disuccinimidyl tartrate; and "Sulfo-DST"-disuccinimidyl tartarate. Again, these linkers are available from Pierce Chemicals.

Examples of non-cleavable linkers are "Sulfo-LC-SMPT"-(sulfosuccinimidyl 6-[alpha-methyl-alpha-(2-pyridylthio) toluamido]hexanoate; "SMPT"; "ABH"-Azidobenzoyl hydrazide; "NHS-ASA"-N-Hydroxysuccinimidyl-4-azidosalicyclic acid; "SASD"-Sulfosuccinimidyl 2-(p-azidosalicylamido)ethyl-1,3-dithiopropionate; "APDP"-N-[4-(p-azidosalicylamido) butyl]-3'(2'-pyidyldithio) propionamide; "BASED"-Bis-[beta-(4-azidosalicylamido) ethyl] disulfide; "HSAB"-N-hydroxysuccinimidyl-4-azidobenzoate; "APG"-p-Azidophenyl glyoxal monohydrate; "SANPAH"-N-Succiminidyl-6(4'-azido-2'-mitrophenylamimo)hexanoate; "Sulfo-SANPAH"-Sulfosuccinimidyl 6-(4'-azido-2'-nitrophenylamino)hexanoate; "ANB-NOS"-N-5-Azido-2-nitrobenzoyloxysuccinimide; "SAND"-Sulfosuccinimidyl-2-(m-azido-o-mitrobenzamido)-ethyl-1,3'-dithiopropionate; "PNP-DTP"-p-nitrophenyl-2-diazo-3,3,3-trifluoropropionate; "SMCC"-Succinimidyl 4-(N-maleimidomethyl)cyclohexane-1-carboxylate; "Sulfo-SMCC"-Sulfosuccinimidyl 4-(N-maleimidomethyl) cyclohexane-1-carboxylate; "MBS"-m-Maleimidobenzoyl-N-hydroxysuccinimide ester; "sulfo-MBS"-m-Maleimidobenzoyl-N-hydroxysulfosuccinimide ester; "SIAB"-N-Succinimidyl (4-iodoacetypaminobenzoate; "Sulfo-SIAB"-N-Sulfosuccinimidyl(4-iodoacetyl)aminobenzoate; "SMPB"-Succinimidyl 4-(p-malenimidophenyl)butyrate; "Sulfo-SMPB"-Sulfosuccinimidyl 4-(p-malenimidophenyl) butyrate; "DSS"-Disuccinimidyl suberate; "BSSS"-bis(sulfosuccinimidyl) suberate; "BMH"-Bis maleimidohexane; "DFDNB"-1,5-difluoro-2,4-dinitrobenzene; "DMA"-dimethyl adipimidate 2 HCl; "DMP"-Dimethyl pimelimidate-2HCl; "DMS"-dimethyl suberimidate-2-HCl; "SPDP"-N-succinimidyl-3-(2-pyridylthio)propionate; "Sulfo HSAB"-Sulfosuccinimidyl 4-(p-azidophenyl)butyrate; "Sulfo-SAPB"-Sulfosuccinimidyl 4-(p-azidophenylbutyrate); "ASIB"-1-9p-azidosalicylamido)-4-(iodoacetamido)butane; "ASBA"-4-(p-Azidosalicylamido)butylamine. All of these linkers are available from Pierce Chemicals.

In another embodiment the linker is a small molecule such as a peptide linker. In one embodiment the peptide linker is not cleavable. In a further embodiment the peptide linker is cleavable by base, under reducing conditions, or by a specific enzyme. In one embodiment, the enzyme is indigenous. Alternatively, the small peptide may be cleavable by a non-indigenous enzyme which is administered after or in addition to the therapeutic complex. Alternatively, the small peptide may be cleaved under reducing conditions, for example, when the peptide contains a disulfide bond. Alternatively, the small peptide may be pH sensitive. Examples of peptide linkers include: poly(L-Gly), (Poly L-Glycine linkers); poly (L-Glu), (Poly L-Glutamine linkers); poly(L-Lys), (Poly L-Lysine linkers). In one embodiment, the peptide linker has the formula (amino acid)$_n$, where n is an integer between 2 and 100, preferably wherein the peptide comprises a polymer of one or more amino acids.

In a further embodiment, the peptide linker is cleavable by proteinase (Suzuki, et al. 1998 *J Biomed Mater Res* 42:112-6). In some embodiments the linker is a cleavable linker comprising, poly(ethylene glycol) (PEG) and a dipeptide, L-alanyl-L-valine (Ala-Val), cleavable by the enzyme thermolysin (Goyal, et al. 2000 *Biochem J* 345:247-254).

The chemical and peptide linkers can be bonded between the Eph receptor binding compound and the therapeutic agent by techniques known in the art for conjugate synthesis, i.e. using genetic engineering, or chemically. The conjugate synthesis can be accomplished chemically via the appropriate antibody by classical coupling reactions of proteins to other moieties at appropriate functional groups. Examples of the functional groups present in proteins and utilized normally for chemical coupling reactions are outlined as follows. The carbohydrate structures may be oxidized to aldehyde groups that in turn are reacted with a compound containing the group H$_2$NNH—R (wherein R is the compound) to the formation of a C=NH—NH—R group. The thiol group (cysteines in proteins) may be reacted with a compound containing a thiol-reactive group to the formation of a thioether group or disulfide group. The free amino group (at the amino terminus of a protein or on a lysine) in amino acid residues may be reacted with a compound containing an electrophilic group, such as an activated carboxy group, to the formation of an amide group. Free carboxy groups in amino acid residues may be transformed to a reactive carboxy group and then reacted with a compound containing an amino group to the formation of an amide group.

The therapeutic agent that is linked to the Eph receptor binding compound could be any chemical, molecule, or complex which effects a desired result. Examples include, but are not limited to, conventional pharmaceutical agents such as antibiotics, anti-neoplastic agents, immunosuppressive agents, hormones, and the like, one or more genes, antisense oligonucleotides, small interfering RNA, contrast agents, proteins, toxins, radioactive molecules or atoms, surfactant proteins, nanoparticles, or clotting proteins. The therapeutic agent may be lipophilic, a quality which will help it enter the targeted cell.

The contrast agents may be any type of contrast agent known to one of skill in the art. The most common contrast agents basically fall into one of four groups; X-ray reagents, radiography reagents, magnetic resonance imaging agents, quantum dots, nanoparticles, and ultrasound agents. The X-ray reagents include ionic, iodine-containing reagents as well as non-ionic agents such as Omnipaque (Nycomed) and Ultravist (Schering). Radiographic agents include radioisotopes as disclosed below. Magnetic Resonance Imaging reagents include magnetic agents such a Gadolinium and iron-oxide chelates. Ultrasound agents include microbubbles of gas and a number of bubble-releasing formulations.

The radionuclides may be diagnostic or therapeutic. Examples of radionuclides that are generally medically useful include: Y, Ln, Cu, Lu, Tc, Re, Co, Fe and the like such as $^{90}$Y, $^{111}$Ln, $^{67}$Cu, $^{77}$Lu, $^{99}$Tc and the like, preferably trivalent cations, such as $^{90}$Y and $^{111}$Ln.

Radionuclides that are suitable for imaging organs and tissues in vivo via diagnostic gamma scintillation photometry include the following: γ-emitting radionuclides: $^{111}$Ln, $^{113m}$Ln, $^{67}$Ga, $^{68}$Ga, $^{99m}$Tc, $^{51}$Cr, $^{197}$Hg, $^{203}$Hg, $^{169}$Yb, $^{85}$Sr, and $^{87}$Sr. The preparation of chelated radionuclides that are suitable for binding by Fab' fragments is taught in U.S. Pat. No. 4,658,839 (Nicoletti et al.) which is incorporated herein by reference.

Paramagnetic metal ions, suitable for use as imaging agents in MRI include the lanthanide elements of atomic number 57-70, or the transition metals of atomic numbers 21-29, 42 or 44. U.S. Pat. No. 4,647,447 (Gies et al.) teaches MRI imaging via chelated paramagnetic metal ions and is incorporated herein by reference.

Examples of therapeutic radionuclides are the β-emitters. Suitable β-emitters include $^{67}$Cu, $^{186}$Rh, $^{188}$Rh, $^{189}$Rh, $^{153}$Sm, $^{90}$Y, and $^{111}$Ln.

Antisense oligonucleotides have a potential use in the treatment of any disease caused by overexpression of a normal gene, or expression of an aberrant gene. Antisense oligonucleotides can be used to reduce or stop expression of that gene. Examples of oncogenes which can be treated with antisense technology and references which teach specific antisense molecules which can be used include: c-Jun and cFos (U.S. Pat. No. 5,985,558, herein incorporated by reference); HER-2 (U.S. Pat. No. 5,968,748, herein incorporated by reference) E2F-1 (Popoff, et al. U.S. Pat. No. 6,187,587; herein incorporated by reference), SMAD 1-7 (U.S. Pat. Nos. 6,159,697; 6,013,788; 6,013,787; 6,013,522; and 6,037,142, herein incorporated by reference), and Fas (Dean et al. U.S. Pat. No. 6,204,055, herein incorporated by reference).

Also provided are double-stranded RNA molecules for use in RNA interference methods in the treatment of any disease caused by overexpression of a normal gene, or expression of an aberrant gene. RNA interference (RNAi) is a process of sequence-specific gene silencing by post-transcriptional RNA degradation, which is initiated by double-stranded RNA (dsRNA) homologous in sequence to the silenced gene. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each 3' end (Elbashir et al. 2001 *Nature* 411:494-498; Bass, 2001 *Nature* 411:428-429; Zamore, 2001 *Nat Struct Biol* 8:746-750). dsRNAs of about 25-30 nucleotides have also been used successfully for RNAi (Karabinos et al. 2001 *PNAS* 98:7863-7868). dsRNA can be synthesized in vitro and introduced into a cell by methods known in the art. By such methods, translation of the target polypeptide can be decreased.

Proteins which may be used as therapeutic agents include apoptosis inducing agents such as pRB and p53 which induce apoptosis when present in a cell (Xu et al. U.S. Pat. No. 5,912,236, herein incorporated by reference), and proteins which are deleted or underexpressed in disease such as erythropoietin (Sytkowski, et al. U.S. Pat. No. 6,048,971, herein incorporated by reference)

It will be appreciated that the therapeutic agent can be any chemotherapeutic agent for neoplastic diseases such as alkylating agents (nitrogen mustards, ethylenimines, alkyl sulfonates, nitrosoureas, and triazenes), antimetabolites (folic acid analogs such as methotrexate, pyrimidine analogs, and purine analogs), natural products and their derivatives (antibiotics, alkaloids, enzymes), hormones and antagonists (adrenocorticosteroids, progestins, estrogens), and the like. Alternatively, the therapeutic agent can be an antisense oligonucleotide which acts as an anti-neoplastic agent, or a protein which activates apoptosis in a neoplastic cell.

The therapeutic agent can be any type of neuroeffector, for example, neurotransmitters or neurotransmitter antagonists may be targeted to an area where they are needed without the wide variety of side effects commonly experienced with their use.

The therapeutic agent can be an anesthetic such as an opioid, which can be targeted specifically to the area of pain. Side effects, such as nausea, are commonly experienced by patients using opioid pain relievers. The method of the present invention would allow the very specific localization of the drug to the area where it is needed, such as a surgical wound or joints in the case of arthritis, which may reduce the side effects.

The therapeutic agent can be an anti-inflammatory agent such as histamine, $H_1$-receptor antagonists, and bradykinin. Alternatively, the anti-inflammatory agent can be a non-steroidal anti-inflammatory such as salicylic acid derivatives, indole and indene acetic acids, and alkanones. Alternatively, the anti-inflammatory agent can be one for the treatment of asthma such as corticosteroids, cromollyn sodium, and nedocromil. The anti-inflammatory agent can be administered with or without the bronchodilators such as $B_2$-selective adrenergic drugs and theophylline.

The therapeutic agent can be a diuretic, a vasopressin agonist or antagonist, angiotensin, or renin which specifically effect a patient's blood pressure.

The therapeutic agent can be any pharmaceutical used for the treatment of heart disease. Such pharmaceuticals include, but are not limited to, organic nitrites (amyl nitrites, nitroglycerin, isosorbide dinitrate), calcium channel blockers, antiplatelet and antithrombotic agents, vasodilators, vasoinhibitors, anti-digitalis antibodies, and nodal blockers.

The therapeutic agent can be any pharmaceutical used for the treatment of protozoan infections such as tetracycline, clindamycin, quinines, chloroquine, mefloquine, trimethoprimsulfamethoxazole, metronidazole, and oramin. The ability to target pharmaceuticals or other therapeutics to the area of the protozoal infection is of particular value due to the very common and severe side effects experienced with these antibiotic pharmaceuticals.

The therapeutic agent can be any anti-bacterial such as sulfonamides, quinolones, penicillins, cephalosporins, aminoglycosides, tetracyclines, chloramphenicol, erythromycin, isoniazids and rifampin.

The therapeutic agent can be any pharmaceutical agent used for the treatment of fungal infections such as amphotericins, flucytosine, miconazole, and fluconazole.

The therapeutic agent can be any pharmaceutical agent used for the treatment of viral infections such as acyclovir, vidarabine, interferons, ribavirin, zidovudine, zalcitabine, reverse transcriptase inhibitors, and protease inhibitors. It can also be envisioned that virally infected cells can be targeted and killed using other therapeutic agent, such as toxins, radioactive atoms, and apoptosis-inducing agents.

The therapeutic agent can be chosen from a variety of anticoagulant, anti-thrombolytic, and anti-platelet pharmaceuticals.

It will be appreciated that diseases resulting from an over- or under-production of hormones can be treated using such therapeutic agent as hormones (growth hormone, androgens, estrogens, gonadotropin-releasing hormone, thyroid hormones, adrenocortical steroids, insulin, and glucagon). Alternatively, if the hormone is over-produced, antagonists or antibodies to the hormones may be used as the therapeutic agent.

Various other possible therapeutic agents include vitamins, enzymes, and other under-produced cellular components and toxins such as diphtheria toxin or botulism toxin.

Alternatively, the therapeutic agent may be one that is typically used in in vitro diagnostics. Thus, the ligand and linker are labeled by conventional methods to form all or part of a signal generating system. The ligand and linker can be covalently bound to radioisotopes such as tritium, carbon 14, phosphorous 32, iodine 125 and iodine 131 by methods well known in the art. For example, 125I can be introduced by procedures such as the chloramine-T procedure, enzymatically by the lactoperoxidase procedure or by the prelabeled Bolton-Hunter technique. These techniques plus others are discussed in H. Van Vunakis and J. J. Langone, Eds, *Methods in Enzymology*, Vol. 70, Part A, 1980. See also U.S. Pat. Nos. 3,646,346, and 4,062,733, both of which are herein incorporated by reference, for further examples of radioactive labels.

Alternatively, the therapeutic agent can be a prodrug or a promolecule which is converted into the corresponding pharmaceutical agent by a change in the chemical environment or by the action of a discrete molecular agent, such as an enzyme. Preferably, the therapeutic agent is administered with the specific molecule needed for conversion of the promolecule. Alternatively, the promolecule can be cleaved by a natural molecule found in the microenvironment of the target tissue. Alternatively, the prodrug is pH sensitive and converted upon change in environment from the blood to the cell or intracellular vesicles (Greco et al. 2001 *J Cell Physiol* 187:22-36).

An effective amount of conjugate that is administered to the mammal can range from about 0.001 mg to about 50 mg/kg of body weight per day. The effective amount will depend on factors, including but not limited to, the route by which the conjugate is administered, binding affinity of the conjugate, Eph receptor expression level in target cells, and Eph receptor expression level in nontarget cells. It will be appreciated, however, that determination of an effective amount of agonist can be readily determined by one of ordinary skill in the art.

Another aspect of the present invention includes pharmaceutical compositions comprising, as an active ingredient, at least one of the peptides, peptidomimetics or small molecules disclosed herein in association with a pharmaceutical carrier or diluent. These compounds can be administered by oral, pulmonary, parenteral (intramuscular, intraperitoneal, intravenous, or subcutaneous injection), inhalational (via a fine powder formulation, or aerosol), transdermal, nasal, vaginal, rectal, or sublingual routes of administration and can be formulated in dosage forms appropriate for each route of administration. See, for example, Bernstein, et al. PCT Patent Publication No. WO 93/25221; Pitt, et al. PCT Patent Publication No. WO 94/17784; and Pitt, et al. European Patent Application 613,683, each of which is incorporated herein by reference.

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, for example, lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose". Amounts effective for this use will depend on the severity of the disease and the weight and general state of the patient.

The compositions described herein can also be microencapsulated by, for example, the method of Tice and Bibi (in: *Treatise on Controlled Drug Delivery*, ed. A. Kydonieus, Marcel Dekker, N.Y. 1992, pp. 315-339), which is hereby incorporated by reference in its entirety.

In prophylactic applications, compositions containing the compounds disclosed herein are administered to a patient susceptible to or otherwise at risk of a particular disease. Such an amount is defined to be a "prophylactically effective dose". In this use, the precise amounts again depend on the patient's state of health and weight, and can be readily determined by one of ordinary skill in the art.

The quantities of the Eph receptor agonist necessary for effective therapy will depend upon many different factors, including means of administration, target site, physiological state of the patient, and other medications administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, for example, in: Gilman, et al. (eds.), 1990 *Goodman and Gilman's: The Pharmacological Basis of Therapeutics* 8th ed., Pergamon Press; and *Remington's Pharmaceutical Sciences*, 7th Ed., Mack Publishing Co., Easton, Pa. (1985), each of which is hereby incorporated by reference.

The peptides and peptidomimetics described herein are effective in treating Eph receptor mediated conditions when administered at a dosage range of from about 0.001 mg to about 50 mg/kg of body weight per day. The specific dose employed is regulated by the particular condition being treated, the route of administration as well as by the judgment of the attending clinician depending upon factors such as the severity of the condition, the age and general condition of the patient, and the like. Such doses can be readily determined by those of skill in the art.

For parenteral administration, the peptides can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (for example, sodium chloride, mannitol) and chemical stability (for example, buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions described herein can be administered as a single dose or in multiple doses; administered either as individual therapeutic agents or in combination with other therapeutic agents; and combined with conventional therapies, which may be administered sequentially or simultaneously.

The compounds can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLO). Many methods for the preparation of such formulations are generally known to those skilled in the art.

The Eph receptor binding compounds described herein can be formulated into a pharmaceutical composition wherein the compound is the only active agent therein. Alternatively, the pharmaceutical composition can contain additional active agents. For example, two or more Eph receptor binding compounds described herein may be used in combination. Moreover, the peptide compound can be combined with one or more other agents that have modulatory effects on Eph receptor activity.

Use of Phage Display to Identify Peptides that Bind Selectively to Eph Family Members Phage display can be used to isolate peptides that specifically bind to each of the sixteen known Eph receptors. As described herein, several phage displayed peptides that specifically bind EphB1, EphB2, EphB3 or EphB4 have been isolated, many of which bind selectively. Accordingly, panning random peptide libraries against members of the Eph receptor family can be used to obtain peptides that bind selectively to an Eph receptor of interest. The clones can be identified by sequencing techniques well known in the art. The length of the peptides contained in the peptide libraries can be modulated to obtain peptides that possess both high binding selectivity and high binding affinity.

Other Utility

The compounds described herein are useful in vitro as unique tools for understanding the biological role of Eph receptors, including the evaluation of the many factors thought to influence, and be influenced by, the production of ephrin ligands and the receptor binding process. The present compounds are also useful in the development of other compounds that bind to and activate Eph receptors, because the present compounds provide important information on the relationship between structure and activity to facilitate such development.

The compounds are also useful as competitive binders in assays to screen for new Eph receptor agonists. In such assay embodiments, the compounds described herein can be used without modification or can be modified in a variety of ways; for example, by labeling, such as covalently or non-covalently joining a moiety which directly or indirectly provides a detectable signal. In any of these assays, the materials thereto can be labeled either directly or indirectly. Possibilities for direct labeling include label groups such as: radiolabels such as $^{125}I$, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups. The compounds may also include spacers or linkers in cases where the compounds are to be attached to a solid support.

Nuclear magnetic resonance (NMR) spectroscopy is known for its ability to characterize macromolecular structures, and is a technique for investigating both static and transient features of ligand binding to a target molecule (Pellecchia, et al. 2002 *Nature Rev Drug Disc* 1:211). NMR spectroscopy is a useful tool for determining the binding of ligands to target molecules, and has the advantage of being able to detect and quantify interactions with high sensitivity without requiring prior knowledge of protein function. Furthermore, NMR spectroscopy can provide structural information on both the target and the ligand to aid subsequent optimization of weak-binding hits into high-affinity leads.

Methods of detecting binding of a ligand compound to a target biomolecule by generating first and second nuclear magnetic resonance correlation spectra from target biomolecules which have been uniformly labeled are reported in U.S. Pat. Nos. 5,698,401 and 5,804,390. The first spectrum is generated from data collected on the target substance in the absence of ligands, and the second in the presence of one or more ligands. A comparison of the two spectra permits determination of Which compounds in the mixture of putative ligands bind(s) to the target biomolecule.

Eph receptors may be selectively labeled by incorporation of $^1H$, $^{13}C$, $^{15}N$ and/or $^{19}F$ into the side chain of one or more amino acid residues. Selectively labeled complexes of an Eph receptor bound to an Eph receptor binding ligand can be exposed to a second molecule and any molecular interaction can be examined by NMR spectroscopy. For example, 2D 13C, 1H-HMQC (heteronuclear multiple quantum coherence) and 13C-edited 1H,1H-NOESY NMR experiments can be used to detect molecular interaction and to determine the dissociation constant for any complex. In addition, a predictive model can be created based on the three-dimensional structure of the target and from the relative position of the ligand with respect to the labeled side chain. The use of several different labeled side-chains in a single, selectively-labeled, target-molecule will improve the resolution as well as the predictive nature of the model.

Because non-peptidic small molecules may be more suitable than peptides for clinical development, High Throughput Screening can be used to screen chemical libraries for small molecules that disrupt the Eph-ephrin complex. The assay uses immobilized Eph receptor ectodomains in complex with ephrin-alkaline phosphatase fusion proteins. The ability to decrease bound alkaline phosphatase activity will identify small molecule inhibitors of the Eph-ephrin interaction.

Moreover, based on their ability to selectively bind to Eph receptors, the peptides described herein can be used as reagents for selectively detecting Eph receptors on living cells, fixed cells, in biological fluids, in tissue homogenates, in purified, natural biological materials, etc. For example, by labeling peptides described herein, one can selectively identify cells having receptors such as EphB1, EphB2, EphB3 or EphB4 on their surfaces. In addition, based on their ability to bind Eph receptors, the peptides can be used in in situ staining, FACS (fluorescence-activated cell sorting), Western blotting, ELISA, etc. In addition, based on their ability to selectively bind Eph receptors, the peptides can be used in receptor purification, or in purifying cells expressing only specific Eph receptors on the cell surface (or inside permeabilized cells).

The compounds described herein can also be utilized as commercial reagents for various medical research and diagnostic uses. Such uses include but are not limited to: (1) use as a calibration standard for quantitating the activities of candidate Eph agonists in a variety of functional assays; (2) use to maintain the proliferation and growth of Eph-dependent cell lines; (3) use in structural analysis of the Eph-receptor ligand-binding interfaces through co-crystallization; (4) use to investigate the mechanism of Eph signal transduction/receptor activation; (5) other research and diagnostic applications wherein the Eph-receptor is preferably activated or such activation is conveniently calibrated against a known quantity of an Eph agonist, and the like; and (6) other research and diagnostic applications wherein the Eph-receptor is preferably inhibited or such inhibition is conveniently calibrated against a known quantity of an Eph antagonist, and the like.

Example 1

Identification of Peptides that Bind to Different EphB Receptors

To identify EphB receptor-binding peptides, an M13 phage library (R&D Systems, Minneapolis, Minn.) displaying random 12 amino acid-long peptides was panned on the ectodomains of EphB1, EphB2, or EphB4 fused to human Fc and immobilized on nickel-coated wells through a carboxy-terminal hexahistidine tag (FIG. 1). Phage binding to Ni-NTA wells coated with 1 μg/ml Eph receptor Fc fusion proteins was quantified using an anti-phage antibody conjugated to horse-radish peroxidase (M13 phage detection kit, Amersham Biosciences) with 2,2-azino-bis(3-ethylbenzothiazoline-6-sulfonic acid) as a substrate. The background that was subtracted from the measurements was determined without EphB4 Fc. Histidine-tagged EphB ectodomain Fc fusion proteins were incubated overnight at 4° C. in nickel-nitrilotriacetic acid (Ni-NTA)-coated ELISA wells at concentrations of 10 μg/ml in Tris-buffered saline (TBS) (150 mM NaCl, 50 mM Tris-HCl, pH 7.5), except for EphB2 and EphB4 rounds 3.2 and 4, which were with 1 μg/ml. Wells were blocked for 1 hour with 0.5% bovine serum albumin (BSA) in TBS, and rinsed with binding buffer (TBS, 1 mM $CaCl_2$, 0.1% Tween-20 or 0.5% Tween-20 for EphB2 and EphB4 rounds 3.2 and 4). In round 1 of panning, $2\times10^{11}$ plaque forming units (PFUs) of the phage library in 100 μl binding buffer were incubated for 1 hour at room temperature in the EphB receptor-coated wells. After washing, remaining bound phage were eluted for 10 min with 100 μl of 0.2 M glycine-HCl, pH 2.2, and neutralized with 15 μl of 1 M Tris-HCl, pH 9. The entire eluate was used to infect early-log phase ER2738 host bacteria and amplified for 4.5 hours at 37° C. The phage were concentrated and stored according to the manufacturer's recommendations. In following rounds $2 \times 10^{11}$ PFUs of the amplified phage pool from the previous round were added to an EphB Fc-coated well and a BSA coated well. The phage were panned as described for round 1, except eluted phage were titered prior to amplification to assess enrichment. Phage recovered after the first round of panning (1*) were not quantified to ensure that rare clones would be recovered.

Two panning experiments were performed for EphB4. The first is shown in FIG. 1A and the second as FIG. 1D. Two experiments were preformed because the first panning experiment, FIG. 1C, yielded receptor-binding phage clones displaying only three different sequences (Table 1). Phage PFUs (plaque forming units) are shown for rounds 2 to 4, and error bars indicate standard deviation. In the EphB1 panning (A), only the blue plaques from peptide-displaying phage were counted in rounds 3 and 4 because there were many white plaques (indicative of phage not displaying any peptide). In the EphB2 panning (B) and the second EphB4 panning, round 3 was repeated twice from round 2 using two different concentrations of receptor ectodomain for coating the wells: 10 µg/ml for round 3.1 and 1 µg/ml for round 3.2. In round 4 for EphB2 and EphB4 (performed using phage from round 3.2), the wells were coated with 1 µg/ml receptor. In all other rounds, 10 µg/ml receptor were used for coating.

Individual phage clones from different rounds of panning were confirmed to bind to the EphB receptor used for their isolation, sequenced to identify the displayed peptides, and named based on the initial 4 or 5 amino acids in their sequence (Table 1). The binding selectivity of the phage clones for the different mammalian EphB receptors was also determined (Table 1). Interestingly, many of the clones identified by panning on EphB1 or EphB2 bind to both receptors, whereas the clones isolated by panning on EphB4 all bind to this receptor with high selectivity. Consistent with this, an alignment of the peptide sequences (Table 1) shows similarities between the EphB1- and EphB2-binding peptides, while the EphB4-binding peptides have more divergent sequences. For example, the THWK phage clone identified by panning on EphB1 and all but one of the clones isolated by panning on EphB2 display related peptides that contain the motif HW (Table 1). This motif is not present in any of the EphB4-binding phage clones. Interestingly, the EWLS EphB1-specific clone contains the sequence SPNL, which is found in the G-H loop of ephrin-B2 and ephrin-B3, and the EphB4-binding TNYL and FSPQ peptides contain the sequences FSPN and FSP, respectively, which are found in the G-H loop of ephrin-B1 and ephrin-B2. Two other EphB4-binding clones (DALN and DHNH) contain the sequence NxWxL (where x is a non-conserved amino acid), which is present in the G-H loop of ephrin-B2 and ephrin-B3. Other EphB4-binding clones were aligned in correspondence of only the carboxy-terminal half of the ephrin G-H loop. Binding curves obtained using different phage concentrations indicate that these clones have lower binding avidity for EphB4.

Example 2

Different Peptides Compete with Each Other for Binding to the EphB Receptor Used for their Isolation To determine whether different phage clones target overlapping Eph receptor binding sites, the EWLS EphB1-binding peptide and the TNYL EphB4-binding peptide were chemically synthesized. These peptides were chosen because they contain sequence motifs found in the ephrins and they bind specifically to EphB1 or EphB4, respectively, when displayed on phage (Table 1). Peptides were synthesized using Fmoc (N-(9-fluorenyl)methoxycarbonyl) chemistry and purified by high pressure liquid chromatography. Biotinylated peptides were synthesized with a carboxy-terminal GSGSK linker with biotin attached to the lysine side chain or with a carboxy-terminal GSGS sequence linked to a carboxy-terminal N-biotinyl-N'-Fmoc-ethylenediamine (Novabiochem). Matrix-assisted laser desorption ionization-time of flight mass spectrometry was used to verify proper peptide synthesis, and purity. Stock solutions of the peptides were dissolved in phosphate buffered saline (PBS, Irvine Scientific) and the pH was verified to be ~6.5. The WHWT peptide had low solubility in aqueous buffers and was therefore solubilized in 15% DMSO in PBS. Peptide concentrations were calculated based on $(O)_{280}$.

The SNEW EphB2-binding peptide, which is one of the few peptides identified that binds with high selectivity to EphB2 was also synthesized and displayed on multiple phage clones (Table 1). Several other peptides were also synthesized. They were chosen based on a combination of criteria, including: (i) the sequence similarity of the peptide to the ephrin-B G-H loop; (ii) the number of phage clones isolated displaying that peptide; and (iii) representation of different sequence motifs (Table 1).

To measure peptide competition of phage binding to EphB receptors, Ni-NTA wells coated with Eph ectodomain Fc were incubated for 30 min at room temperature with various peptide concentrations in binding buffer (100 µl/well). Concentrated stocks of phage clones diluted between 1:500 and 1:10,000 in binding buffer were then added to the wells for a 1 hr at room temperature. Wells were washed and bound phage were detected using the anti-M13 antibody. A biotinylated control peptide with sequence unrelated to the sequences of the Eph-binding peptides (RTVAHHGGLYHTNAEVK, SEQ ID NO: 40) was used as a negative control in some of the experiments, as indicated in the figure legends.

To measure the specificity of peptide binding to Eph receptors, biotinylated peptides were immobilized on streptavidin-coated plates at 10 µM (Pierce Biotechnology, Rockford, Ill.) and incubated for 1 hr with different Eph ectodomain Fc fusion proteins at 2.5 µg/ml in binding buffer. Bound receptor was detected using an anti-Fc antibody coupled to alkaline phosphatase (Promega) with p-nitrophenylphosphate as substrate (Pierce). The background that was subtracted from the measurements was determined by omitting the Eph ectodomain.

Figure 2:
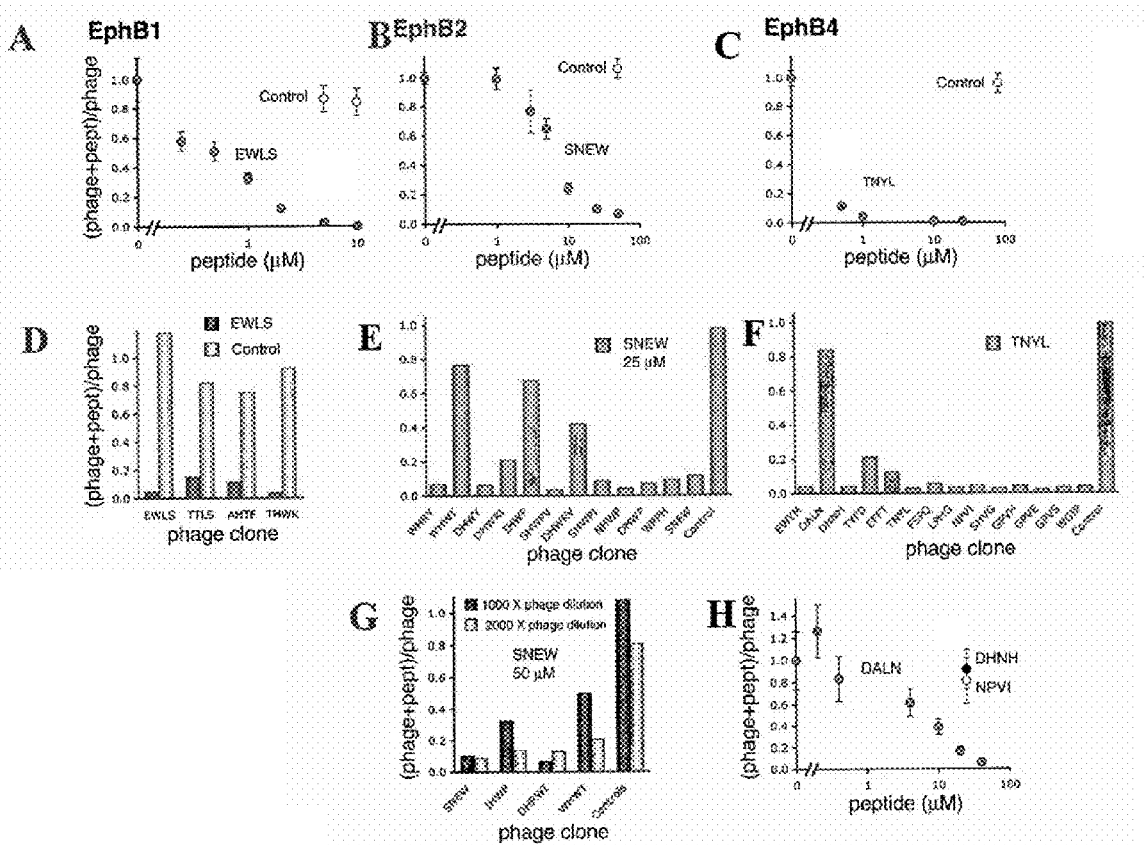
FIGS. 2A-H are charts showing competition between peptides for binding to EphB receptors. (A) The EWLS peptide inhibits binding of EWLS phage to the immobilized EphB1 ectodomain in a concentration-dependent manner. (B) The SNEW peptide inhibits binding of SNEW phage to the immobilized EphB2 ectodomain in a concentration-dependent manner. (C), the TNYL peptide inhibits binding of TNYL phage to the immobilized EphB4 ectodomain in a concentration-dependent manner. (D) The EWLS peptide inhibits EphB1 binding of the phage clones isolated by panning on EphB1. (E) and (G) the SNEW peptide inhibits EphB2 binding of most phage clones isolated by panning on EphB2. (F) The TNYL peptide inhibits binding to EphB4 of the phage clones isolated by panning on EphB4. (H) The DALN peptide inhibits binding of DALN phage to the immobilized EphB4 ectodomain in a concentration-dependent manner. Error bars indicate standard deviation from duplicate measurements, and were calculated taking into account propagation of errors.

The EWLS, SNEW, and TNYL peptides efficiently inhibited binding of the corresponding phage clone to the appropriate immobilized EphB receptor in concentration-dependent manner (FIGS. 2 A, B and C), RTVA (see Example 1) was used as the control peptide.

Each peptide also inhibited binding of all the other phage clones that were isolated using the same EphB receptor (See FIGS. 2D, E, F and G). Specifically, the EWLS peptide at 5 µM inhibited EphB1 binding of the phage clones isolated by panning on EphB1 (FIG. 2D). SNEW was used as the control peptide in both panels. The SNEW peptide at 25 µM inhibited EphB2 binding of most phage clones isolated by panning on EphB2 (FIGS. 2E and G). The only exceptions were the IHWP, DHRWV and WHWT clones. However, binding of these clones was inhibited by 50 µM SNEW peptide, particularly when the phage concentration was halved. RTVA was used as the control peptide with SNEW phage in (E) and SNEW was used as a control with the TNYL EphB4-binding phage in (G). The TNYL peptide at 25 µM inhibited binding to EphB4 of the phage clones that were isolated by panning on EphB4, except for the DALN clone (FIG. 2F). The SWL EphA2-binding peptide (Koolpe, M. et al. 2002 *J Biol Chem* 277:46974-46979) was used as the control peptide in (C) and (F). The DALN peptide (but not the DHNH and NPVI peptides) inhibited binding of DALN phage to the immobilized EphB4 ectodomain in a concentration-dependent manner (FIG. 2H). Bound phage were detected using anti-M13 phage antibody coupled to HRP and phage binding in the presence of peptide was normalized to phage binding in the absence of peptide. Error bars indicate standard deviation from duplicate measurements, and were calculated taking into account propagation of errors.

These results indicate that all but one of the peptides identified by panning on an EphB receptor bound to the same region of that receptor. Based on the sequence similarity of some of the peptides with the ephrin G-H loop, the common binding site presumably corresponds to the ephrin high-affinity binding interface of the Eph receptors.

Example 3

Figure 3:
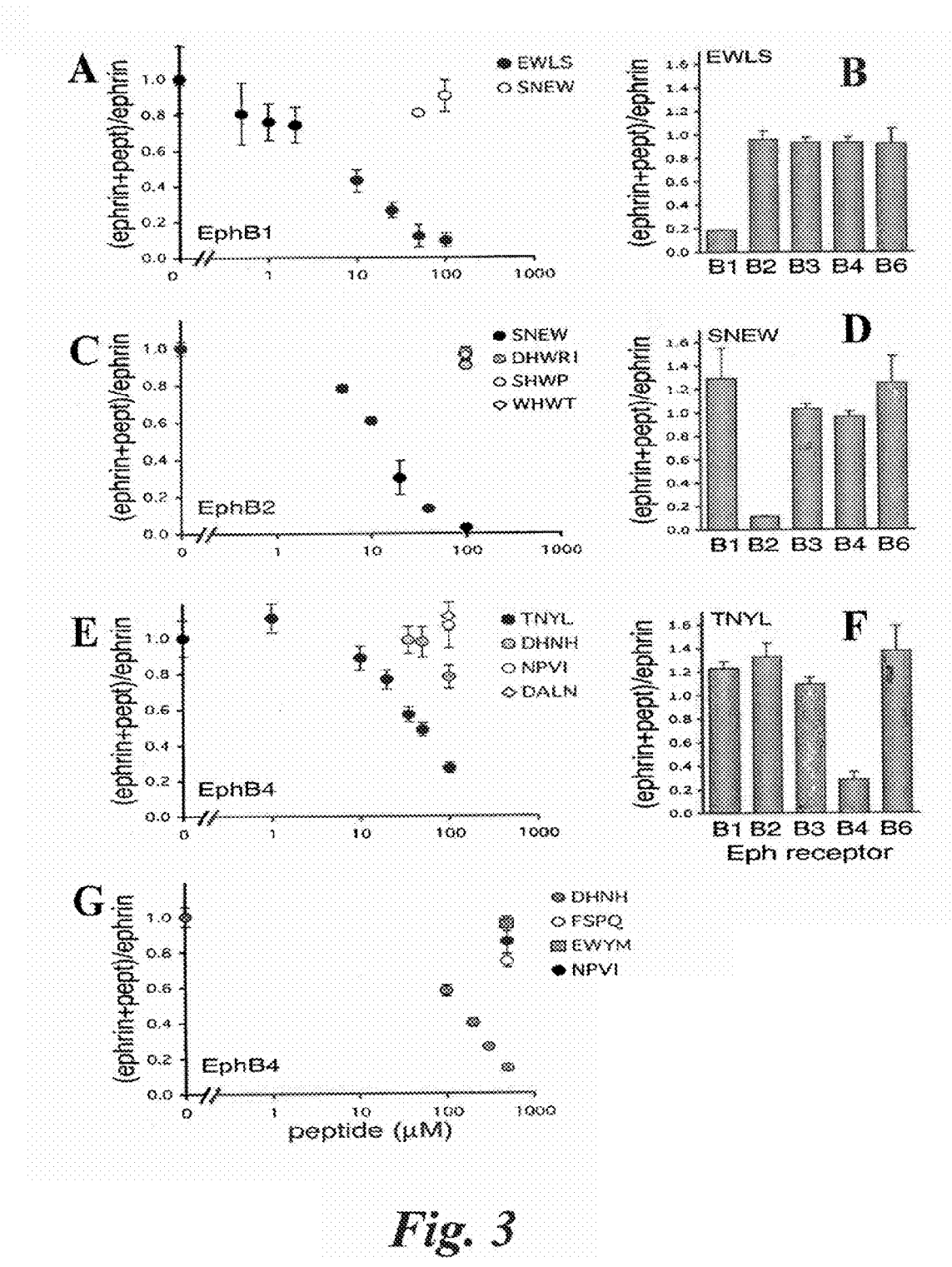
FIGS. 3A-G are charts showing peptides that selectively antagonize ephrin-B2 binding to EphB receptors. (A, C, E, and G) Ephrin-B2 AP binding to the indicated immobilized EphB receptor ectodomains detected by measuring alkaline phosphatase activity. (B, D, and F) different EphB ectodomains incubated with ephrin-B2 AP and the indicated peptides. Error bars indicate standard deviation from duplicate measurements, and were calculated taking into account propagation of errors.

Peptides that Selectively Antagonize Ephrin Binding to the EphB1, EphB2, and EphB4 Receptors Peptides that bind to the same receptor region as the ephrins would be expected to inhibit Eph receptor-ephrin association, if they interact with sufficient affinity. A number of synthetic peptides were tested for their ability to inhibit binding of alkaline phosphatase-tagged ephrin-B2 (ephrin-B2-AP) to EphB receptors (FIG. 3). Most of the peptides were synthesized with a biotin tag and immobilized on streptavidin plates to verify their ability to capture the EphB ectodomains used for their isolation.

Ephrin-B2 AP binding to the indicated immobilized EphB receptor ectodomains was measured in the presence of the indicated peptides and detected by measuring alkaline phosphatase activity. Of the peptides tested for their ability to inhibit ephrin binding to EphB receptors, EWLS and AHTF inhibited ephrin binding to EphB1; SNEW (but not DHWRI, SHWP, or SHWT) inhibited ephrin binding to EphB2; and both TNYL and DHNH (but not NPVI or DALN) inhibited ephrin binding to EphB4 (FIGS. 3A, C, E, and G). The concentration of biotinylated peptides necessary to inhibit binding of the dimeric ephrin-B2 AP by 50% ($IC_{50}$) was approximately 10 μM for EWLS, 150 μl for AHTF, 15 μM for SNEW, 50 μM for TNYL, and 200 μM for DHNH (FIGS. 3 A, C, E, and G, and Table 1). The $IC_{50}$ values for the EWLS and SNEW peptides synthesized without the carboxy-terminal biotinylated linker were similar, whereas the $IC_{50}$ for the non-biotinylated TNYL peptide was substantially higher than for biotinylated TNYL (150 μM). Wells coated with the different EphB ectodomains were incubated with ephrin-B2 AP and 50 μM of the indicated peptides. Ephrin-B2 AP binding in the presence of peptide was normalized to binding in the absence of peptide. All peptides were biotinylated except for FSPQ and EWYM. Only the IPWT peptide failed to bind the EphB receptor (EphB4), presumably because its affinity is too low. Therefore, IPWT was not used for further experiments. The EWYM, TWO, and FSPQ peptides were not synthesized with a biotin tag and therefore were tested directly for inhibition of ephrin-B2 binding. The EWLS, SNEW, and TNYL peptides were selective because they antagonized ephrin binding to only one EphB receptor (FIGS. 3B, D, and F). In contrast, the AHTF peptide inhibited ephrin-binding to several EphB receptors.

Example 4

The SNEW Peptide Inhibits EphB2 Signaling and Biological Effects

Figure 4:
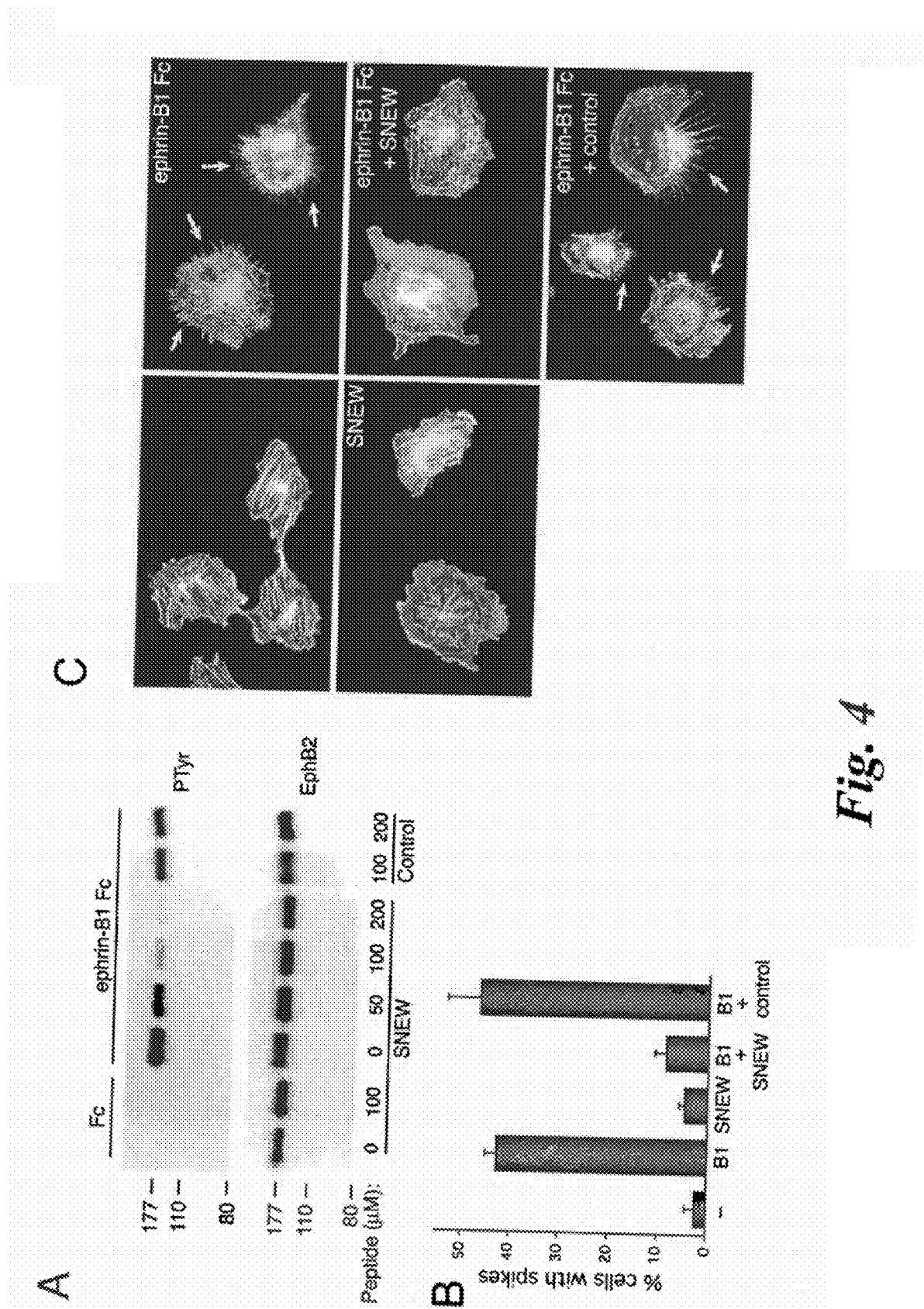
FIGS. 4A and 4B are charts showing that the SNEW peptide antagonizes ephrin-induced activation of endogenous EphB2 in COS cells. (A) The SNEW peptide antagonizes ephrin-B1 Fc-induced tyrosine phosphorylation (activation) of EphB2 in a concentration-dependent manner. (B) The SNEW peptide antagonizes ephrin-B 1 Fc-induced retraction of COS cells. Quantitation of the percent of cells with spikes with and without ephrin-B1 Fc (B1) and in the presence or in the absence of 400 μM SNEW peptide. (C) Representative examples of the cell morphologies.

Preincubation of COS cells with the SNEW peptide in a concentration-dependent manner blocked the ability of ephrin-B1 Fc to induce tyrosine phosphorylation, and therefore activation, of endogenous EphB2 (FIG. 4A). EphB2 was immunoprecipitated from COS cells after stimulation with ephrin-B1 Fc, or Fc as a control, in the presence of the indicated concentrations of SNEW peptide and control RTVA peptide. For EphB2 immunoprecipitations, COS cells were serum-starved in DME high glucose for 3 hrs prior to stimulation with 1 μg/ml ephrin-B1 Fc or Fc protein in the presence or absence of EphB2-binding peptides or a control peptide. For EphB4 immunoprecipitations, MCF-7 cells were stimulated with 0.5 μg/ml ephrin-B2 Fe or Fe protein in the presence or absence of the TNYL-RAW peptide. After ephrin stimulation, the cells were lysed in modified RIPA buffer (150 mM NaCl, 1 mM EDTA, 1% Triton X-100, 1% Na deoxycholate, 0.1% SDS, 20 mM Tris pH 8.0) with protease inhibitors and 1 mM sodium orthovanadate. Cell lysates were used for immunoprecipitation with either 5 μg EphB2 antibodies or 10 μg EphB4 antibodies. The immunoprecipitates were eluted by boiling in 2×SDS sample buffer, separated by SDS-polyacrylamide gel electrophoresis and probed by immunoblotting with peroxidase-conjugated anti-phosphotyrosine antibody (Transduction Laboratories, San Diego, Calif.). The immunoblots were then stripped and reprobed with either EphB2 antibody or a monoclonal EphB4 antibody (Zymed) followed by a secondary anti-rabbit IgG or anti-mouse peroxidase-conjugated antibody.

The filters were probed by immunoblotting with anti-phosphotyrosine antibodies (PTyr) and reprobed with EphB2 antibodies to confirm equal amounts of immunoprecipitated receptor.

Furthermore, SNEW inhibited the COS cell retraction phenotype that occurred when EphB2 signaling was stimulated by ephrin-B1 Fc (FIG. 4B, C). Upon treatment with 1.5 μg/ml ephrin-B1 Fc, COS cells retract at the periphery, leaving behind spike-like protrusions. Quantitation of the percent of cells with spikes with and without ephrin-B1 Fc (B1) and in the presence or in the absence of 400 μM SNEW peptide is shown in (B). Representative examples of the cell morphologies are shown in (C). COS cells were plated onto glass coverslips and sixteen hours later were starved for three hours in DME with 0.5% fetal calf serum. The cells were then incubated for 20 min with 400 μM SNEW or control peptide in PBS, or an equal volume of PBS as a control, and then either left untreated or stimulated for 10 min with 1.5 μg/ml ephrinB1-Fc (R&D Systems, Inc.). The cells were then fixed in 4% formaldehyde, permeabilized in 0.1% Triton X-100 in PBS, stained with Alexa 594-labeled phalloidin (Molecular Probes), and mounted on glass slides. Control peptide: RTVA. Thus, SNEW can be used to block the biological effects of the EphB2 receptor. In contrast, EWLS at concentrations up to 200 μM did not inhibit endogenous EphB1 tyrosine phosphorylation following ephrin-B1 Fc stimulation of human aortic endothelial cells and TNYL at concentrations up to 350 μM did not inhibit endogenous EphB4 tyrosine phosphorylation following ephrin-B2 Fc stimulation of MCF7 and MDA-MB-231 breast cancer cells.

Example 5

EphB-Binding Peptides as Targeting Agents

Figure 5:
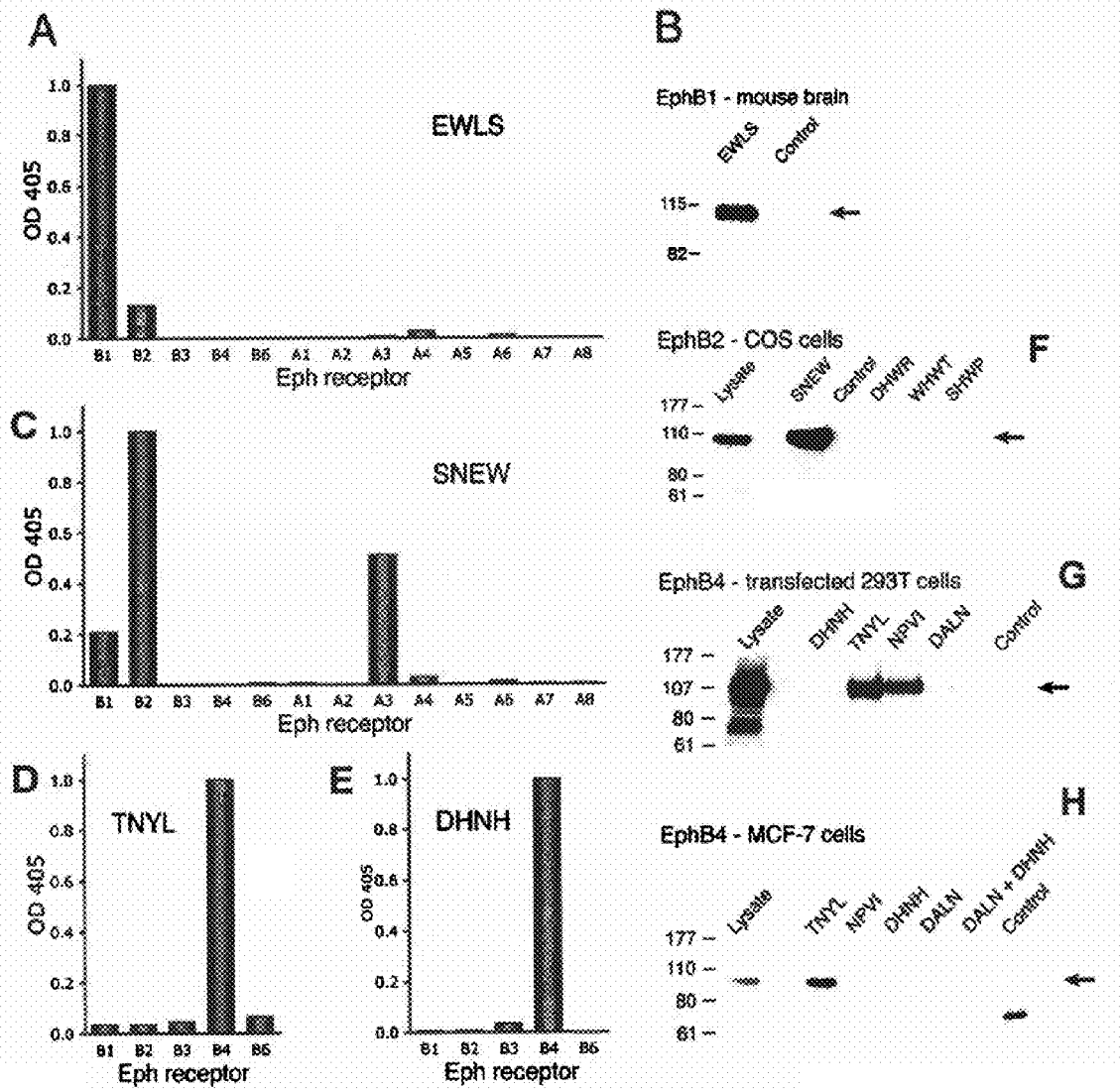
FIGS. 5A-H are charts showing peptides as EphB receptor-targeting agents. (A, C, D and E) Eph receptor binding selectivity of EWLS (A), SNEW (C), TNYL (D) and DHNH (E) peptides. (B, F, G and H) The EWLS, SNEW and TNYL peptides immobilized on streptavidin beads stably bind EphB receptors from tissue and cell lines.

In addition to inhibiting the ability of Eph receptors to bind ephrins and elicit biological responses, EphB-binding peptides can selectively target other molecules, such as drugs or imaging probes, to EphB receptor-expressing cells. A stringent assay to determine the receptor-binding specificity of the peptides used biotinylated peptides immobilized on streptavidin plates, which captured dimeric EphB Fc with high avidity (the apparent dissociation constants are in the low nM range). Biotinylated peptides were immobilized on streptavidin-coated plates and used to capture Eph receptor Fc proteins. Bound receptor was detected using anti-Fc antibody coupled to alkaline phosphatase and was normalized to the value in the well with highest receptor binding. These experiments showed that EWLS and all the EphB4-binding peptides tested bound selectively to EphB1 or EphB4, respectively, and not any other A- or B-class Eph receptors, while SNEW exhibited some binding to EphA3 in addition to EphB2 (FIGS. 5A, C, D and E). In contrast, the AHTF, SHWPI, WHWT, and DHRWI peptides were less specific and exhibited substantial binding to several EphA and EphB receptors.

Example 6

Binding Stability of Peptides

The ability of the peptides to bind in a stable manner, which is important for both targeting and competitive inhibition, was tested in pull-down experiments. For peptide pull-down experiments, cells in 60 cm plates at 70% confluency or adult mouse brain tissue were solubilized in pull-down buffer (50 mM HEPES pH 7.5, 150 mM NaCl, 10% glycerol, 1% Triton-X100, 5 mM KCl and 1 mM EDTA). Three µg of biotinylated peptide were incubated for 45-90 min with 5 µl streptavidin agarose beads (Sigma), unbound peptide was washed away, and the beads were incubated with the cell lysates for 45-90 min. Proteins bound to the beads were separated by SDS-polyacrylamide gel electrophoresis and probed by immunoblotting with EphB1, EphB2, or EphB4 antibodies. The EphB1 antibody (Santa Cruz) was detected with a secondary anti-goat IgG peroxidase-conjugated antibody (BioRad Laboratories). The EphB2 and EphB4 antibodies were affinity-purified polyclonal antibodies to GST fusion proteins containing approximately 100 amino acids from the carboxy-terminal tails of the EphB2 or EphB4 receptors (Noren, N. K. et al. 2004 *PNAS USA* 101:5583-5588; Holash, J. A. & Pasquale, E. B. 1995 *Devel Biol* 172:683-693) and were detected with a secondary anti-rabbit IgG peroxidase-conjugated antibody (Amersham Biosciences).

Endogenous EphB receptors were isolated from lysates of mouse brain or cultured cells using the EWLS, SNEW, and TNYL peptides immobilized on streptavidin beads (FIGS. 5B, F, G and H). The EWLS, SNEW and TNYL peptides immobilized on streptavidin beads stably bind EphB receptors from tissue and cell lines. The NPVI peptide did not detectably bind endogenous EphB4 from the MCF7 breast cancer cell line but bound the more highly expressed EphB4 from transfected 293T human embryonic kidney cells. RTVA was used as a control peptide for the EphB4 pull downs. The NPVI peptide could isolate EphB4 from transfected cells but not endogenous EphB4 from MCF7 cells, which is present at lower levels (FIGS. 5B, F, G and H). These results indicate that EWLS, SNEW, and TNYL dissociate slowly, thus mediating stable binding that persists during the washing steps. EphB receptors were not detected bound to the beads coated with the other peptides. The DALN and DHNH peptides were ineffective when used either alone or together, even though the phage competition experiments suggest that these two peptides bind to distinct sites of EphB4 and might therefore be expected to act synergistically.

Example 7

Peptide Targeting

To demonstrate the targeting ability of EphB receptor-binding peptides, the TNYL peptide was used to mediate binding of fluorescent streptavidin-coated quantum dot nanocrystals to cells expressing transfected as well as endogenous EphB4. For labeling of cells expressing transfected EphB4, COS cells in 6 cm plates were transfected with 3 µg of a plasmid encoding the EphB4 extracellular and transmembrane domains fused to enhanced green fluorescent protein (EGFP) (Ogawa, K. et al. 2000 *Oncogene* 19:6043-6052), or 3 of a vector encoding farnesylated EGFP (pEGFP-F) (BD Biosciences Clontech) as control, using SuperFect transfection reagent. The cells were plated on glass coverslips 1 day after transfection and labeled 2 days after transfection. For labeling experiments, 20 nM streptavidin-conjugated Qdot 655 quantum dots (Quantum Dot Corp.) were preincubated with 500 nM biotinylated TNYL peptide for 20 min on ice in quantum-dot-binding-buffer (1 mM $CaCl_2$, 2% BSA in PBS). The cells were incubated with quantum dots containing bound TNYL peptide, or quantum dots without peptide as a control, for 20 min at 4° C. and washed with ice cold 1 mM $CaCl_2$ in PBS. For labeling of cells endogenously expressing EphB4, MCF-7 cells plated on glass coverslips coated with fibronectin (10 µg/ml) were incubated with 100 µM biotinylated TNYL peptide diluted in quantum-dot-binding-buffer for 20 min at 4° C. The cells were then washed with ice cold 1 mM $CaCl_2$ in PBS, followed by incubation with 20 nM streptavidin quantum dots for 20 min at 4° C. After labeling, the cells were fixed in 4% formaldehyde/4% sucrose for 10 min and permeabilized for 5 min with 0.05% Triton-X100 in PBS. The nuclei were counterstained with DAPI and the coverslips were mounted with ProLong Gold mounting media (Molecular Probes) onto glass slides and imaged and photographed under a fluorescence microscope. Green fluorescent protein marked the transfected cells. The TNYL Qdots labeled EphB4ΔC-EGFP-transfected cells but not EGFP-transfected cells or untransfected cells.

MCF7 cells, which express endogenous EphB4, were also labeled by quantum dots bound to TNYL but not by control quantum dots without peptide. MCF-7 human breast cancer cells, which endogenously express EphB4, were grown in Minimum Essential medium Eagle (MEM) (ATCC) with 10% fetal bovine serum, 0.01 mg/ml bovine insulin, and Pen/Strep. COS cells, which endogenously express EphB2, and 293 human embryonic kidney (HEK) cells were grown in Dulbecco's Modified Eagles medium (DME) with high glucose (Irvine Scientific) with 10% fetal calf serum, sodium pyruvate, and Pen/Strep. Ten cm plates of 293 HEK cells were transfected with 9 µg EphB4 cDNA in pcDNA3, and 1 µg of an enhanced green fluorescent protein plasmid (BD Biosciences Clontech) to verify transfection efficiency, using SuperFect transfection reagent (Qiagen). The cells were passaged 1 day after transfection and used for pull-down experiments 2 days after transfection. Nuclei of both transfected and untransfected cells were labeled with DAPI. TNYL was shown to be capable of also binding to EphB4 even after fixation of the cells with 4% formaldehyde, indicating that the peptide binding site on the receptor is not disrupted by the fixation procedure.

Example 8

Optimization of the TNYL EphB4-Binding Peptide

Figure 6:
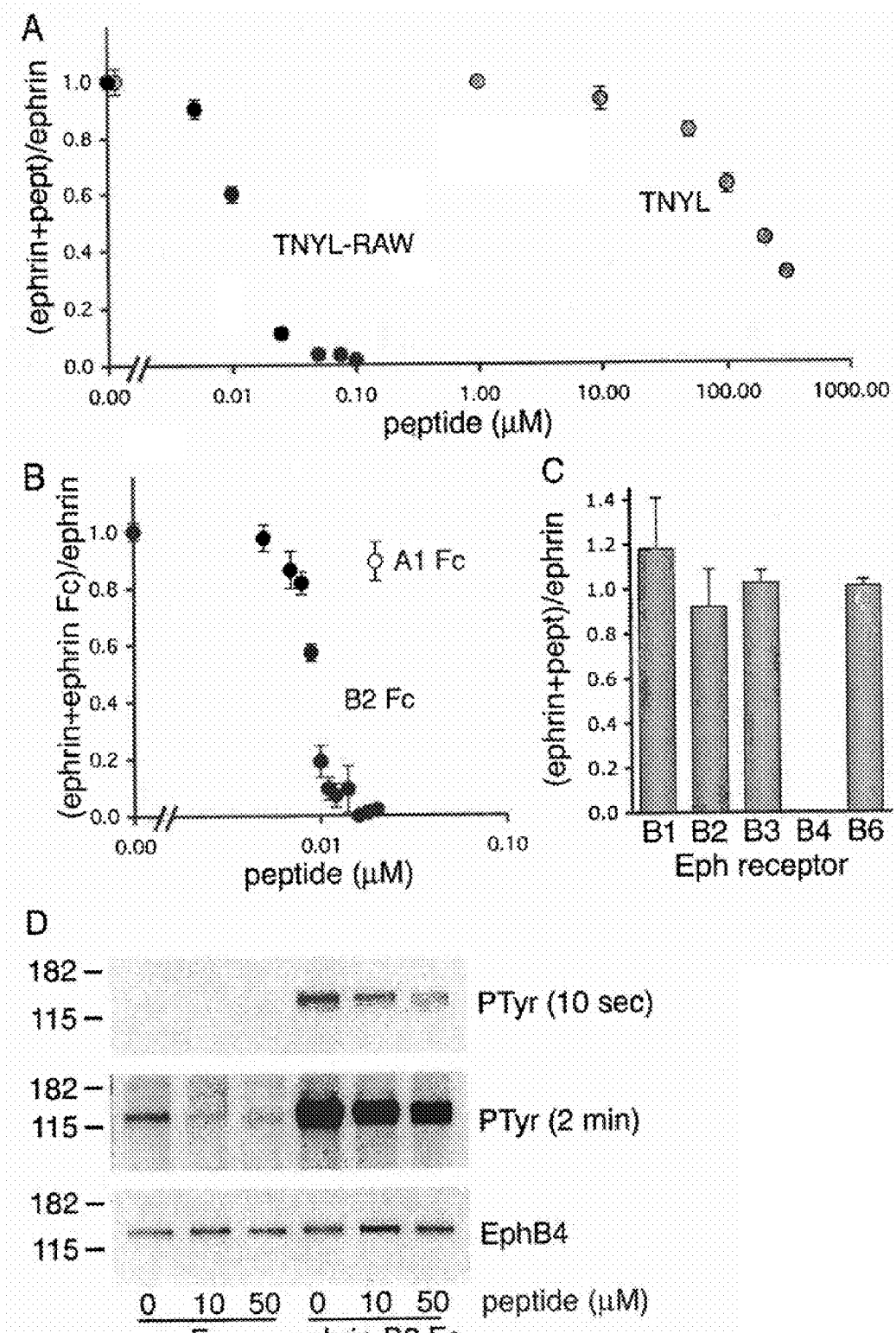
FIGS. 6A-D are charts showing that the TNYL-RAW peptide is a much more potent EphB4 antagonist than TNYL while maintaining selectivity. (A) The TNYL-RAW peptide inhibits binding of ephrin-B2 AP to the immobilized EphB4 ectodomain. Error bars indicate standard deviation from triplicate measurements for TNYL-RAW and from duplicate measurements for TNYL, and were calculated taking into account propagation of errors. (B) Ephrin-B2 Fc inhibits binding of ephrin-B2 AP to the immobilized EphB4 ectodomain. (C) The TNYL-RAW peptide inhibits binding of ephrin-B2 AP to the immobilized EphB4 ectodomain but not other EphB ectodomains. Error bars indicate standard deviation from triplicate measurements, and were calculated taking into account propagation of errors. (D) The TNYL-RAW peptide antagonizes ephrin-B2-induced tyrosine phosphorylation of EphB4 in a concentration-dependent manner.

Inspection of the EphB4-binding peptide sequences revealed the consensus motifs GP (see below) and RAW in the peptides that align in correspondence of the carboxy-terminal portion of the ephrin G-H loop (Table 1). The GP motif aligns with the GP motif of TNYL and the RAW motif aligns precisely next to the last amino acid of TNYL. This suggests that a TNYL peptide containing the RAW consensus motif at its carboxy terminus might bind better to EphB4. For competition assays between peptides and ephrin-B2 alkaline phosphatase fusion protein (ephrin-B2 AP), the concentration of ephrin-B2 AP used was adjusted to obtain similar signals with different EphB receptors (0.135-1.45 OD min$^{-1}$ml$^{-1}$). Ephrin-B2 AP was co-incubated for 1 hr with different peptide concentrations in Ni-NTA wells coated with 1 µg/ml Eph receptor Fc. After several washes, the amount of ephrin-B2-AP bound was quantified using p-nitrophenylphosphate as a substrate. Alkaline phosphatase activity from wells without EphB Fc was subtracted as background. The non-biotinylated form of this TNYL-RAW peptide (TNYLFSPNGPIARAW, SEQ ID NO: 39) was generated and was found to inhibit ephrin-B2 AP binding to EphB4 with an IC$_{50}$ of ~15 nM (FIG. 6A). Remarkably, this value is 10,000 times lower than the IC$_{50}$ of ~150 µM for the non-biotinylated TNYL (FIG. 6A) and comparable to the IC$_{50}$ of ~9 nM for the dimeric ephrin-B2 Fc (FIG. 6B), where Ephrin-A1 Fc was used as a control. In these experiments, the two peptides are not biotinylated. Despite the dramatically increased ability to bind EphB4, the TNYL-RAW peptide retained high selectivity and did not inhibit ephrin-binding to other EphB receptors even at concentrations much higher than those sufficient to inhibit ephrin binding (FIG. 6C), where the TNYL-RAW peptide (10 µM) inhibits binding of ephrin-B2 AP to the immobilized EphB4 ectodomain but not other EphB ectodomains. Ephrin-B2-AP binding in the presence of peptide was normalized to binding in the absence of peptide in (A) and (B). The TNYL-RAW peptide also inhibited in a concentration-dependent manner EphB4 tyrosine phosphorylation induced by ephrin-B2 Fc stimulation of MCF7 cells as well as basal EphB4 tyrosine phosphorylation, which is presumably due to stimulation by low levels of endogenously expressed ephrin-B2 (FIG. 6D). Endogenous EphB4 was immunoprecipitated from MCF7 breast cancer cells after stimulation with ephrin-B2 Fc, or Fc as a control, and probed by immunoblotting with anti-phosphotyrosine antibodies (PTyr). A 10 sec exposure shows that the TNYL-RAW peptide inhibits the phosphorylation of EphB4 induced by ephrin-B2 Fc, whereas a 2 min exposure shows that the peptide also inhibits the low levels of EphB4 phosphorylation that are presumably due to endogenously expressed ephrin-B2. The filters were reprobed with EphB4 antibodies to confirm equal amounts of immunoprecipitated receptor.

Although only some peptides contain amino acids that are conserved in the G-H loop of the B-class ephrin-Bs (italicized and bold Table 1), similarities between the peptides allowed the assembly of an overall alignment (Table 1). The best EphB1- and EphB4-binding peptides identified in the screens, EWLS and TNYL, have four consecutive amino acids in common with the amino-terminal portion of the ephrin G-H loop, which is the portion of the loop that contributes most of the contacts with the Eph receptor (Himanen, J. P et al. 2001 Nature 414:933-938). However, each peptide also has distinctive sequence features, in agreement with its selective binding to only one EphB receptor.

The alignment revealed other interesting features of the peptides. The great majority of the peptides have a proline in correspondence of the tryptophan at the tip of the ephrin G-H loop (Himanen, J. P et al. 2001 Nature 414:933-938). Although proline is not similar to tryptophan, it introduces a bend in the peptides that may mimic the bend at the tip of the G-H loop (Himanen, J. P et al. 2001 Nature 414:933-938). Further supporting the idea that the proline may be structurally important, in many of the EphB4-binding peptides a glycine precedes the proline and it is known that in the appropriate sequence context the glycine-proline (GP) motif greatly stabilizes the structure of short peptides by promoting a β-hairpin structure even in the absence of disulfide bonds (Blanco, F. et al. 1998 Curr Opin Struct Biol 8:107-111; Neidigh, J. W. et al. 2002 Nat Struct Biol 9:425-430; Song, J. et al. Biochemistry 41:10942-10949). The GP motif is known to play a critical role in a high-affinity cyclic peptide that binds to the erythropoietin receptor (Wrighton, N. C. et al. 1996 Science 273:458-464; Livnah, O. et al. 1996 Science 273:464-471). In this erythropoietin-mimic peptide, the GP motif introduces a β-turn structure linking two short β-strands, and it also mediates important contacts with the erythropoietin receptor. Several phage libraries displaying cyclic peptides that contain a central GP motif have been successfully used to identify structurally constrained peptides that bind with high affinity to cell surface receptors (Fairbrother, W. J. et al. 1998 Biochemistry 37:17754-17764; Cwirla, S. E. et al. 1997 Science 276:1696-1699; Lowman, H. B. et al. 1998 Biochemistry 37:8870-8878). Interestingly, the EphB4-binding peptides containing the GP motif were isolated from an unbiased and linear peptide library.

In the EphB1- and EphB2-binding peptides the proline is not preceded by glycine, indicating that the particular type of β-turn induced by the GP motif (Blanco, F. et al. 1998 Curr Opin Struct Biol 8:107-111) is not important for interaction with the binding sites of these other EphB receptors. The THWC EphB2-binding peptide is one of the few peptides that does not contain the conserved proline. However, this peptide is probably a disulfide-bonded cyclic peptide that forms a loop with a tip in correspondence of the tip of the ephrin G-H loop (Himanen, J. P et al. 2001 Nature 414:933-938). This supports the idea that most of the peptides that were identified mimic the G-H loop of the ephrins, albeit through different mechanisms. Finally, instead of the proline found in most other peptides, three of the EphB4-binding peptides contain a tryptophan, which is conserved in the G-H loop of the preferred ligand for EphB4, ephrin-B2 (Bennett, B. D. et al. 1995 PNAS USA 92:1866-1870).

As evidenced above, joining the different sequence motifs was extremely effective in enhancing the binding affinity. The TNYL-RAW peptide inhibited binding of the dimeric ephrin-B2 AP to EphB4 with an IC$_{50}$ value of approximately 15 nM, which indicates that the KD for binding of TNYL-RAW to EphB4 is in the same range as the KDs for monovalent Eph-ephrin interactions (16 nM for EphB2-ephrin-B2 and 10-12 nM for EphA3-ephrin-A5) (Lackmann, M. et al. 1997 J Biol Chem 272:16521-16530; Himanen, J. P. et al. 1998 Nature 396:486-491; Smith, F. M. et al. 2004 J Biol Chem 279:9522-9531). In fact, the IC$_{50}$ value for the dimeric ephrin-B2 Fc is only slightly lower (~9 nM). The potency of TNYL-RAW as an antagonist is remarkable considering the absence of a disulphide bond in this peptide. It indicates that TNYL-RAW must nevertheless have an appropriately restrained conformation to avoid a large loss of entropy upon EphB4 binding, which would compromise the binding affinity.

Many of the peptides identified based on their binding to EphB1 or EphB2, can bind to both receptors (Table 1), indicating that the ephrin-binding pockets of these receptors are closely related. Indeed, the residues of EphB2 that contribute to the high affinity interface with ephrin-B2 (Himanen, J. P et al. 2001 Nature 414:933-938) are highly conserved in EphB1 (85% amino acid identity between the mouse sequences), but not in EphB4 (42% identity). Overall, the ephrin-binding domains of mouse EphB1 and EphB2 are 77% identical to each other, but only 46% and 43% identical to the ephrin-binding domain of mouse EphB4, respectively.

Example 9

Administration of an EphB Receptor-Binding Peptide in the Treatment of Cancer A patient is identified by various diagnostic methods as being in need of treatment for colorectal cancer. A therapeutically effective amount of an EphB receptor-binding peptide is administered to the patient. Following such treatment, a reduction in the colorectal cancer in the patient is found.

Example 10

Administration of an EphB Receptor-Binding Peptide in the Treatment of Cancer A patient is identified by various diagnostic methods as being in need of treatment for a neoplastic disorder associated with abnormal angiogenesis. A therapeutically effective amount of an EphB receptor-binding peptide is administered to the patient prior to surgical and/or chemotherapeutic treatment to reduce neovascularization of the tumor thereby inducing shrinkage of the tumor. Following such treatment, a reduction in the size of the tumor is found.

Example 10

Administration of an EphB Receptor-Binding Peptide in the Treatment of Chronic Pain A patient complaining of neuropathic pain is administered a therapeutically effective amount of an Eph B receptor binding peptide. A reduction in the level of the pain is observed and measured in the patient.

Example 11

Administration of an EphB Receptor-Binding Peptide in the Treatment of Spinal Cord Injury A patient with a spinal cord injury is administered a therapeutically effective amount of an EphB receptor binding peptide that inhibits activity of the EphB receptor. Nerve regeneration at the site of injury is stimulated. Following such treatment, nerve regeneration at the site of stimulation is found in the patient.

TABLE 1

EphB Receptor-Binding Peptides

| Panning Receptor | #clones[a] | SEQ ID NO | Peptide Sequence[b,c] | EphB Receptor Specificity (% Binding)[d] | | | | | Peptide IC$_{50}$[e] |
|---|---|---|---|---|---|---|---|---|---|
| | | | | B1 | B2 | B3 | B4 | B6 | |
| EphB1 | 1[4] | 1 | EWL SPNLAPSVR | 100 | 2 | 1 | 1 | 0 | ~10 μM[f] |
| | 2[3] | 2 | TTLSQ LPKSTWL | 100 | 0 | 1 | 0 | 0 | nd |
| | 16[3,4] | 3 | AHTFP YPHPKPH | 100 | 4 | 8 | 1 | 0 | ~150 μM |
| | 1[3] | 4 | SHKFPGPPSWMS | 88 | 100 | 10 | 9 | 0 | nd |
| | 1[3] | 5 | THWKFQPWALVT | 86 | 100 | 5 | 0 | 0 | nd |
| EphB2 | 1[3,2] | 6 | THWCH LLNCAAL | 100 | 89 | 85 | 20 | 26 | nd |
| | 1[3,1] | 7 | WHRYPDPRMLPT | 54 | 100 | 31 | 13 | 15 | nd |
| | 5[3,2,4] | 8 | WHWTIEPFAITS | 99 | 100 | 22 | 20 | 45 | >100 μM |
| | 1[2] | 9 | DHWYYTPWQPIE | 100 | 81 | 5 | 5 | 2 | nd |
| | 2[2,3,2] | 10 | DHWRI LPFSLSS | 53 | 100 | 4 | 1 | 3 | >100 μM |
| | 1[2] | 11 | IHW PVAPYSYLD | 97 | 100 | 4 | 4 | 7 | nd |
| | 1[2] | 12 | SHW PV LPFAHWQ | 98 | 100 | 9 | 6 | 10 | nd |
| | 5[2,3,2,4] | 13 | DHWRVSPYSLLY | 100 | 97 | 1 | 0 | 1 | nd |
| | 1[4] | 14 | SHW PISPYSLLS | 39 | 100 | 9 | 4 | 8 | >100 μM |
| | 1[2] | 15 | NHW PTQPYAIPI | 18 | 100 | 22 | 22 | 0 | nd |
| | 1[4] | 16 | DHW PL LPYALAH | 4 | 100 | 7 | 0 | 0 | nd |
| | 1[2] | 17 | WPPHW PRSLDYA | 0 | 100 | 0 | 0 | 0 | nd |
| | 3[2] | 18 | SNEWIQ PR LPQH | 1 | 100 | 7 | 1 | 12 | ~15 μM[f] |
| EphB4 | 1[3,2] | 19 | EWYMKFPPE HY F | 22 | 23 | 23 | 100 | 30 | >600 μM |
| | 7[3(1st)] | 20 | DAL ND WL LFRPW | 0 | 0 | 10 | 100 | 16 | >100 μM |
| | 4[3,1,3,2,4] | 21 | DHNHNLY NP WR L | 9 | 8 | 9 | 100 | 7 | ~200 μM |
| | 1[2] | 22 | TY FDFQA WSIRA | 10 | 21 | 18 | 100 | 30 | >50 μM[g] |
| | 1[3,2] | 23 | EFFTWRPTYYGI | 16 | 12 | 29 | 100 | 17 | nd |
| | 5[2,3,1,4] | 24 | TNYL FSPNGPIA | 5 | 3 | 3 | 100 | 7 | ~50 μM[h] |
| | 1[4] | 25 | FSPQGPAARNFA | 13 | 8 | 11 | 100 | 11 | >600 μM |
| | 1[2] | 26 | L PHGPVAAAWDA | 2 | 15 | 2 | 100 | 4 | nd |
| | 1[3,2] | 27 | NPVIGPIQRAWT | 1 | 0 | 4 | 100 | 0 | >500 μM |
| | 1[3,1] | 28 | SHVGPIMRAWAP | 22 | 6 | 2 | 100 | 6 | nd |
| | 1[3,1] | 29 | GPV HRAWEPTSH | 4 | 6 | 16 | 100 | 7 | nd |
| | 2[3,2,4] | 30 | GPVERAWRPDLI | 1 | 2 | 1 | 100 | 3 | nd |
| | 1[3,1] | 21 | GPVSKAWQETET | 13 | 13 | 14 | 100 | 16 | nd |
| | 2[3] | 32 | GPVADAWLVYPR | 10 | 5 | 4 | 100 | 6 | nd |

TABLE 1-continued

EphB Receptor-Binding Peptides

| Panning Receptor | #clones[a] | SEQ ID NO | Peptide Sequence[b,c] | EphB Receptor Specificity (% Binding)[d] | | | | | Peptide IC$_{50}$[e] |
|---|---|---|---|---|---|---|---|---|---|
| | | | | B1 | B2 | B3 | B4 | B6 | |
| | 1[3.1] | 33 | WGIPRAAQVMWT | 16 | 17 | 20 | 100 | 14 | nd |
| | 1[3 (1st)] | 34 | IPWTQ_H_MAMSPM | nd | nd | nd | 100 | nd | nd |
| | 1[3 (1st)] | 35 | SGHQL_L_LNKMPN | nd | nd | nd | 100 | nd | nd |
| Ephrin-B1 | | 36 | KFQ*EFSPNYM*GL*EF*KKHHDY | | | | | | |
| Ephrin-B2 | | 37 | KFQ*EFSPNLW*GL*EF*QKNKDY | | | | | | |
| Ephrin-B3 | | 38 | KFQ*EYSPNLW*GH*EF*RSHHDY | | | | | | |

[a] The round of panning is indicated as a superscript, 1st is the first panning on EphB4.
[b] The names of the peptides that were synthesized are underlined;
[c] The alignment was by eye, and the G-H loop of the human ephrins are underlined.
[d] Values >25 are indicated in bold.
[e] Concentration of peptide required to inhibit ephrin-B2 AP binding by 50%;
[f] Biotinylated and non-biotinylated peptides gave the same result;
[g] Limited by solubility;
[h] This value was obtained with the biotinylated peptide, although the IC$_{50}$ for the non-biotinylated peptide is 150 µM;
nd, not determined.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

---

What is claimed is:

1. An isolated peptide which binds to a member of EphB1 or EphB2 receptor and inhibits binding of Ephrin B ligand to said member of the EphB1 or EphB2 receptor, wherein said peptide consists of less than 25 amino acid residues and has the amino acid sequence of SEQ ID NO: 1, SEQ ID NO: 2, SEQ ID NO: 3, SEQ ID NO: 4, or SEQ ID NO: 5.

2. The isolated peptide of claim 1, wherein said peptide has the amino acid sequence of SEQ ID NO: 1 and selectively binds to EphB1.

3. The isolated peptide of claim 1, wherein said peptide has the amino acid sequence of SEQ ID NO: 2 and selectively binds to EphB1.

4. The isolated peptide of claim 1, wherein said peptide has the amino acid sequence of SEQ ID NO: 3 and selectively binds to EphB1.

5. The isolated peptide of claim 1, wherein said peptide has the amino acid sequence of SEQ ID NO: 4 and binds to EphB1 or EphB2.

6. The isolated peptide of claim 1, wherein said peptide has the amino acid sequence of SEQ ID NO: 5 and binds to EphB1 or EphB2.

7. The isolated peptide of claim 1, in association with a therapeutically acceptable carrier.

8. The isolated peptide of claim 1, wherein said peptide consists of the amino acid sequence of SEQ ID NO: 1, SEQ ID NO: 2, SEQ ID NO: 3, SEQ ID NO: 4, or SEQ ID NO: 5.

9. The isolated peptide of claim 2, wherein said peptide inhibits Ephrin B2 ligand binding to the EphB1 receptor with an $IC_{50}$ value of approximately 10 µM.

10. The isolated peptide of claim 4, wherein said peptide inhibits Ephrin B2 ligand binding to the EphB1 receptor with an $IC_{50}$ value of approximately 150 µM.

11. The isolated peptide of claim 9 or 10, wherein the $IC_{50}$ value is determined by assays to measure the concentration of said peptide necessary to inhibit binding by 50% of alkaline phosphatase-tagged Ephrin B2 ligand to an ectodomain of the EphB1 receptor, wherein alkaline phosphatase-tagged Ephrin B2 ligand binding to the ectodomain of the EphB1 receptor is detected by measuring alkaline phosphatase activity.

12. A conjugate comprising the peptide of claim 1 or claim 8 and a therapeutic agent or imaging agent.

13. The conjugate of claim 12, wherein said therapeutic agent is a chemotherapeutic agent, a toxin, a radioactive molecule, a clotting protein, an immunosuppressive agent, or a hormone.

14. The conjugate of claim 12, wherein said peptide and said therapeutic agent or said imaging agent are conjugated to each other via a linker.

15. The conjugate of claim 12, wherein said imaging agent is a radionuclide or a fluorescent label.

* * * * *

SEQUENCE LISTING

```
<160> NUMBER OF SEQ ID NOS: 40

<210> SEQ ID NO 1
<211> LENGTH: 12
<212> TYPE: PRT
<213> ORGANISM: Artificial Sequence
<220> FEATURE:
<223> OTHER INFORMATION: synthetic peptide

<400> SEQUENCE: 1

Glu Trp Leu Ser Pro Asn Leu Ala Pro Ser Val Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: synthetic peptide

<400> SEQUENCE: 2

Thr Thr Leu Ser Gln Leu Pro Lys Ser Thr Trp Leu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: synthetic peptide

<400> SEQUENCE: 3

Ala His Thr Phe Pro Tyr Pro His Pro Lys Pro His
1               5                   10
```

```
<210> SEQ ID NO 4
<211> LENGTH: 12
<212> TYPE: PRT
<213> ORGANISM: Artificial Sequence
<220> FEATURE:
<223> OTHER INFORMATION: synthetic peptide

<400> SEQUENCE: 4

Ser His Lys Phe Pro Gly Pro Pro Ser Trp Met Ser
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: synthetic peptide

<400> SEQUENCE: 5

Thr His Trp Lys Phe Gln Pro Trp Ala Leu Val Thr
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: synthetic peptide

<400> SEQUENCE: 6

Thr His Trp Cys His Leu Leu Asn Cys Ala Ala Leu
 1               5                  10

<210> SEQ ID NO 7
<211> LENGTH: 12
<212> TYPE: PRT
<213> ORGANISM: Artificial Sequence
<220> FEATURE:
<223> OTHER INFORMATION: synthetic peptide

<400> SEQUENCE: 7

Trp His Arg Tyr Pro Asp Pro Arg Met Leu Pro Thr
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: synthetic peptide

<400> SEQUENCE: 8

Trp His Trp Thr Ile Glu Pro Phe Ala Ile Thr Ser
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: synthetic peptide

<400> SEQUENCE: 9

Asp His Trp Tyr Tyr Thr Pro Trp Gln Pro Ile Glu
 1               5                  10
```

```
<210> SEQ ID NO 10
<211> LENGTH: 12
<212> TYPE: PRT
<213> ORGANISM: Artificial Sequence
<220> FEATURE:
<223> OTHER INFORMATION: synthetic peptide

<400> SEQUENCE: 10

Asp His Trp Arg Ile Leu Pro Phe Ser Leu Ser Ser
  1               5                  10

<210> SEQ ID NO 11
<211> LENGTH: 12
<212> TYPE: PRT
<213> ORGANISM: Artificial Sequence
<220> FEATURE:
<223> OTHER INFORMATION: synthetic peptide

<400> SEQUENCE: 11

Ile His Trp Pro Val Ala Pro Tyr Ser Tyr Leu Asp
  1               5                  10

<210> SEQ ID NO 12
<211> LENGTH: 12
<212> TYPE: PRT
<213> ORGANISM: Artificial Sequence
<220> FEATURE:
<223> OTHER INFORMATION: synthetic peptide

<400> SEQUENCE: 12

Ser His Trp Pro Val Leu Pro Phe Ala His Trp Gln
  1               5                  10

<210> SEQ ID NO 13
<211> LENGTH: 12
<212> TYPE: PRT
<213> ORGANISM: Artificial Sequence
<220> FEATURE:
<223> OTHER INFORMATION: synthetic peptide

<400> SEQUENCE: 13

Asp His Trp Arg Val Ser Pro Tyr Ser Leu Leu Tyr
  1               5                  10

<210> SEQ ID NO 14
<211> LENGTH: 12
<212> TYPE: PRT
<213> ORGANISM: Artificial Sequence
<220> FEATURE:
<223> OTHER INFORMATION: synthetic peptide

<400> SEQUENCE: 14

Ser His Trp Pro Ile Ser Pro Tyr Ser Leu Leu Ser
  1               5                  10

<210> SEQ ID NO 15
<211> LENGTH: 12
<212> TYPE: PRT
<213> ORGANISM: Artificial Sequence
<220> FEATURE:
<223> OTHER INFORMATION: synthetic peptide

<400> SEQUENCE: 15

Asn His Trp Pro Thr Gln Pro Tyr Ala Ile Pro Ile
  1               5                  10

<210> SEQ ID NO 16
<211> LENGTH: 12
```

```
<212> TYPE: PRT
<213> ORGANISM: Artificial Sequence
<220> FEATURE:
<223> OTHER INFORMATION: synthetic peptide

<400> SEQUENCE: 16

Asp His Trp Pro Leu Leu Pro Tyr Ala Leu Ala His
1               5                   10

<210> SEQ ID NO 17
<211> LENGTH: 12
<212> TYPE: PRT
<213> ORGANISM: Artificial Sequence
<220> FEATURE:
<223> OTHER INFORMATION: synthetic peptide

<400> SEQUENCE: 17

Trp Pro Pro His Trp Pro Arg Ser Leu Asp Tyr Ala
1               5                   10

<210> SEQ ID NO 18
<211> LENGTH: 12
<212> TYPE: PRT
<213> ORGANISM: Artificial Sequence
<220> FEATURE:
<223> OTHER INFORMATION: synthetic peptide

<400> SEQUENCE: 18

Ser Asn Glu Trp Ile Gln Pro Arg Leu Pro Gln His
1               5                   10

<210> SEQ ID NO 19
<211> LENGTH: 12
<212> TYPE: PRT
<213> ORGANISM: Artificial Sequence
<220> FEATURE:
<223> OTHER INFORMATION: synthetic peptide

<400> SEQUENCE: 19

Glu Trp Tyr Met Lys Phe Pro Pro Glu His Tyr Phe
1               5                   10

<210> SEQ ID NO 20
<211> LENGTH: 12
<212> TYPE: PRT
<213> ORGANISM: Artificial Sequence
<220> FEATURE:
<223> OTHER INFORMATION: synthetic peptide

<400> SEQUENCE: 20

Asp Ala Leu Asn Asp Trp Leu Leu Phe Arg Pro Trp
1               5                   10

<210> SEQ ID NO 21
<211> LENGTH: 12
<212> TYPE: PRT
<213> ORGANISM: Artificial Sequence
<220> FEATURE:
<223> OTHER INFORMATION: synthetic peptide

<400> SEQUENCE: 21

Asp His Asn His Asn Leu Tyr Asn Pro Trp Arg Leu
1               5                   10

<210> SEQ ID NO 22
<211> LENGTH: 12
<212> TYPE: PRT
<213> ORGANISM: Artificial Sequence
```

```
<220> FEATURE:
<223> OTHER INFORMATION: synthetic peptide

<400> SEQUENCE: 22

Thr Tyr Phe Asp Phe Gln Ala Trp Ser Ile Arg Ala
1               5                   10

<210> SEQ ID NO 23
<211> LENGTH: 12
<212> TYPE: PRT
<213> ORGANISM: Artificial Sequence
<220> FEATURE:
<223> OTHER INFORMATION: synthetic peptide

<400> SEQUENCE: 23

Glu Phe Phe Thr Trp Arg Pro Thr Tyr Tyr Gly Ile
1               5                   10

<210> SEQ ID NO 24
<211> LENGTH: 12
<212> TYPE: PRT
<213> ORGANISM: Artificial Sequence
<220> FEATURE:
<223> OTHER INFORMATION: synthetic peptide

<400> SEQUENCE: 24

Thr Asn Tyr Leu Phe Ser Pro Asn Gly Pro Ile Ala
1               5                   10

<210> SEQ ID NO 25
<211> LENGTH: 12
<212> TYPE: PRT
<213> ORGANISM: Artificial Sequence
<220> FEATURE:
<223> OTHER INFORMATION: synthetic peptide

<400> SEQUENCE: 25

Phe Ser Pro Gln Gly Pro Ala Ala Arg Asn Phe Ala
1               5                   10

<210> SEQ ID NO 26
<211> LENGTH: 11
<212> TYPE: PRT
<213> ORGANISM: Artificial Sequence
<220> FEATURE:
<223> OTHER INFORMATION: synthetic peptide

<400> SEQUENCE: 26

Leu Pro His Gly Pro Val Ala Ala Trp Asp Ala
1               5                   10

<210> SEQ ID NO 27
<211> LENGTH: 12
<212> TYPE: PRT
<213> ORGANISM: Artificial Sequence
<220> FEATURE:
<223> OTHER INFORMATION: synthetic peptide

<400> SEQUENCE: 27

Asn Pro Val Ile Gly Pro Ile Gln Arg Ala Trp Thr
1               5                   10

<210> SEQ ID NO 28
<211> LENGTH: 12
<212> TYPE: PRT
<213> ORGANISM: Artificial Sequence
<220> FEATURE:
<223> OTHER INFORMATION: synthetic peptide
```

```
<400> SEQUENCE: 28

Ser His Val Gly Pro Ile Met Arg Ala Trp Ala Pro
 1               5                  10

<210> SEQ ID NO 29
<211> LENGTH: 12
<212> TYPE: PRT
<213> ORGANISM: Artificial Sequence
<220> FEATURE:
<223> OTHER INFORMATION: synthetic peptide

<400> SEQUENCE: 29

Gly Pro Val His Arg Ala Trp Glu Pro Thr Ser His
 1               5                  10

<210> SEQ ID NO 30
<211> LENGTH: 12
<212> TYPE: PRT
<213> ORGANISM: Artificial Sequence
<220> FEATURE:
<223> OTHER INFORMATION: synthetic peptide

<400> SEQUENCE: 30

Gly Pro Val Glu Arg Ala Trp Arg Pro Asp Leu Ile
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: synthetic peptide

<400> SEQUENCE: 31

Gly Pro Val Ser Lys Ala Trp Gln Glu Thr Glu Thr
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: synthetic peptide

<400> SEQUENCE: 32

Gly Pro Val Ala Asp Ala Trp Leu Val Tyr Pro Arg
 1               5                  10

<210> SEQ ID NO 33
<211> LENGTH: 12
<212> TYPE: PRT
<213> ORGANISM: Artificial Sequence
<220> FEATURE:
<223> OTHER INFORMATION: synthetic peptide

<400> SEQUENCE: 33

Trp Gly Ile Pro Arg Ala Ala Gln Val Met Trp Thr
 1               5                  10

<210> SEQ ID NO 34
<211> LENGTH: 12
<212> TYPE: PRT
<213> ORGANISM: Artificial Sequence
<220> FEATURE:
<223> OTHER INFORMATION: synthetic peptide

<400> SEQUENCE: 34
```

Ile Pro Trp Thr Gln His Met Ala Met Ser Pro Met
1               5                   10

<210> SEQ ID NO 35
<211> LENGTH: 11
<212> TYPE: PRT
<213> ORGANISM: Artificial Sequence
<220> FEATURE:
<223> OTHER INFORMATION: synthetic peptide

<400> SEQUENCE: 35

Ser Gly His Gln Leu Leu Asn Lys Met Pro Asn
1               5                   10

<210> SEQ ID NO 36
<211> LENGTH: 20
<212> TYPE: PRT
<213> ORGANISM: Artificial Sequence
<220> FEATURE:
<223> OTHER INFORMATION: synthetic peptide

<400> SEQUENCE: 36

Lys Phe Gln Glu Phe Ser Pro Asn Tyr Met Gly Leu Glu Phe Lys Lys
1               5                   10                  15

His His Asp Tyr
            20

<210> SEQ ID NO 37
<211> LENGTH: 20
<212> TYPE: PRT
<213> ORGANISM: Artificial Sequence
<220> FEATURE:
<223> OTHER INFORMATION: synthetic peptide

<400> SEQUENCE: 37

Lys Phe Gln Glu Phe Ser Pro Asn Leu Trp Gly Leu Glu Phe Gln Lys
1               5                   10                  15

Asn Lys Asp Tyr
            20

<210> SEQ ID NO 38
<211> LENGTH: 20
<212> TYPE: PRT
<213> ORGANISM: Artificial Sequence
<220> FEATURE:
<223> OTHER INFORMATION: synthetic peptide

<400> SEQUENCE: 38

Lys Phe Gln Glu Tyr Ser Pro Asn Leu Trp Gly His Glu Phe Arg Ser
1               5                   10                  15

His His Asp Tyr
            20

<210> SEQ ID NO 39
<211> LENGTH: 15
<212> TYPE: PRT
<213> ORGANISM: Artificial Sequence
<220> FEATURE:
<223> OTHER INFORMATION: synthetic peptide

<400> SEQUENCE: 39

Thr Asn Tyr Leu Phe Ser Pro Asn Gly Pro Ile Ala Arg Ala Trp
1               5                   10                  15

<210> SEQ ID NO 40

```
<211> LENGTH: 17
<212> TYPE: PRT
<213> ORGANISM: Artificial Sequence
<220> FEATURE:
<223> OTHER INFORMATION: synthetic peptide

<400> SEQUENCE: 40

Arg Thr Val Ala His His Gly Gly Leu Tyr His Thr Asn Ala Glu Val
 1               5                  10                  15

Lys
```